United States Patent [19]

Sherry et al.

[11] Patent Number: 5,316,757

[45] Date of Patent: May 31, 1994

[54] SYNTHESIS OF POLYAZAMACROCYCLES WITH MORE THAN ONE TYPE OF SIDE-CHAIN CHELATING GROUPS

[75] Inventors: A. Dean Sherry, Dallas, Tex.; Jeroen van Westrenen, Amsterdam, Netherlands

[73] Assignee: Board of Regents, The University of Texas System, Austin, Tex.

[21] Appl. No.: 808,845

[22] Filed: Dec. 13, 1991

Related U.S. Application Data

[63] Continuation-in-part of Ser. No. 615,619, Nov. 19, 1990, which is a continuation-in-part of Ser. No. 357,193, May 25, 1989, abandoned, and a continuation-in-part of Ser. No. 291,053, Dec. 28, 1988, Pat. No. 4,983,376, Continuation-in-part of Ser. No. 7,729, Jan. 27, 1987, which is a continuation-in-part of Ser. No. 662,075, Oct. 18, 1984, Pat. No. 4,639,365.

[51] Int. Cl.$^5$ .................... A61K 49/02; C07F 9/38
[52] U.S. Cl. ........................... 424/9; 540/465; 514/79; 514/185
[58] Field of Search ............. 540/465, 474; 534/15, 534/16; 424/9; 514/79, 185

[56] References Cited

U.S. PATENT DOCUMENTS

| 2,205,995 | 6/1940 | Ulrich et al. | 558/455 |
|---|---|---|---|
| 3,930,867 | 1/1976 | Bigelow | 540/465 |
| 3,932,451 | 1/1976 | Bigelow | 540/465 |
| 3,987,128 | 10/1976 | Richman | 424/9 |
| 3,996,276 | 12/1976 | Atkins | 540/465 |
| 4,038,312 | 7/1977 | Atkins | 540/465 |
| 4,085,106 | 4/1978 | Atkins | 540/465 |
| 4,130,715 | 12/1978 | Atkins | 540/465 |
| 4,337,154 | 6/1982 | Fukuchi | 210/490 |
| 4,352,751 | 10/1982 | Wieder | 552/540 |
| 4,421,671 | 12/1983 | Cusano | 252/301.4 |
| 4,432,907 | 2/1984 | Wieder | 552/540 |
| 4,472,509 | 9/1984 | Gansow | 424/1.1 |
| 4,639,365 | 1/1987 | Sherry | 424/9 |
| 4,647,447 | 3/1987 | Gries et al. | 424/9 |
| 4,702,998 | 10/1987 | Tanaka et al. | 540/454 |
| 4,731,239 | 3/1988 | Gordon | 424/9 |
| 4,735,796 | 4/1988 | Gordon | 424/9 |
| 4,889,931 | 12/1989 | Rocklage et al. | 540/465 |
| 4,957,939 | 9/1990 | Gries et al. | 424/9 |
| 4,963,344 | 10/1990 | Gries et al. | 424/9 |
| 4,983,376 | 1/1991 | Sherry | 540/474 |

FOREIGN PATENT DOCUMENTS 232751 8/1987 European Pat. Off. ............ 540/474

(List continued on next page.)

OTHER PUBLICATIONS

Miller, et al. Chem. Ber. 25, 1892 pp. 2020–2045.

(List continued on next page.)

Primary Examiner—Mukund J. Shah
Assistant Examiner—P. K. Sripada
Attorney, Agent, or Firm—Arnold, White & Durkee

[57] ABSTRACT

The pH controlled selectivity of the sulfomethylation reaction is used to prepare a series of di-, tri-, tetra- and hexaazacyclomacrocycles with specified patterns of pendent side-chain chelating groups. The prepared mono and diacetic acid derivatives, together with monomethylenephosphonate and monomethylenephosphinate derivatives of tetraazacyclododecane, and triazcyclododecane and [9]aneN3, make these types of ligands easily available by a synthetic pathway that avoids the use of protective groups. The invention thus comprises a variety of compounds, methods and uses characterized by relatively high synthetic yields of polyazamacrocyclic ligands exhibiting a wide and predictable choice of metal ion binding constants water and lipid solubilities by reason of their substituent pendent groups.

11 Claims, 21 Drawing Sheets

FOREIGN PATENT DOCUMENTS

| | | | |
|---|---|---|---|
| 0287465A1 | 10/1988 | European Pat. Off. | C07D 257/02 |
| 0374929A1 | 6/1990 | European Pat. Off. | |
| 0448191A1 | 9/1991 | European Pat. Off. | 540/465 |
| 0485045A2 | 5/1992 | European Pat. Off. | 540/465 |
| 3129906 | 7/1981 | Fed. Rep. of Germany | 424/9 |
| 3401052 | 1/1989 | Fed. Rep. of Germany | 424/9 |
| 2539996 | 1/1984 | France | 424/9 |
| 1081169 | 3/1984 | U.S.S.R. | 540/474 |
| 1529150 | 9/1977 | United Kingdom | 540/474 |
| 2137612 | 1/1984 | United Kingdom | 540/474 |

OTHER PUBLICATIONS

Cabbiness et al., "Macrocyclic Effect on the Stability of Copper(II) Tetramine Complexes", *J. Am. Chem. Soc.*, *91*(23):6540 (1969).

Martin et al., "The Relationship between Metal-Donor Distance and Ring Size in Macrocyclic Complexes", *J. Am. Chem. Soc.*, *96*(12):4046 (1974).

Richman et al., "Nitrogen Analogs of Crown Ethers", *J. Am. Chem. Soc.*, *96*(7):2268-70 (1974).

Lettvin et al., *J. Mag. Res.*, 28:459-61 (1977).

White et al., *J. Amer. Chem. Soc.*, 101(17):4921 (1979).

Desreux, *Inorganic Chemistry*, 19:1319-24 (1980).

Sherry, "A Proposal on Basic Chemical Research," submitted to the Robert A. Walsh Foundation (1981).

Bryden et al., *Chemical Abstracts*, No. 97:206960z (1982).

Desreux, letter dated Dec. 23, 1983 to Sherry.

Brasch et al., *A.J.R.*, 142:625-30 (1984).

Chen et al, *Fed. Euro. Biochem. Soc.*, 168(1):70 (1984).

Goldstein et al., *Physiol. Chem. & Phys. & Med. NMR*, *16*:97-104 (1984).

Sherry, letter dated Apr. 4, 1984 to Schmidt.

Weinmann et al., *A.J.R.*, 142:619-24 (1984).

Wolf, *Physiol. Chem. & Phys. & Med. NMR, 16*:93-95 (1984).

Geraldes et al., *Inorganic Chemistry, 24*(23):3876 (1985).

Geraldes et al., *Journal of Magnetic Resonance, 66*:274-82 (1986).

Geraldes et al., *Magnetic Resonance in Medicine, 3*:242-50 (1986).

Sherry et al., *Journal of Magnetic Resonance, 66*:511-24 (1986).

Chavez et al., *J. Org. Chem., 54*(12):2990-92 (1989).

Sherry, *J. Less Common Metals, 149*:133-41 (1989).

The *Chemical Abstracts* citation of European Patent Application EP 382,582, 16 Aug. 1990 to Parker et al.

European Patent Application EP 382,582, published Aug. 16, 1990.

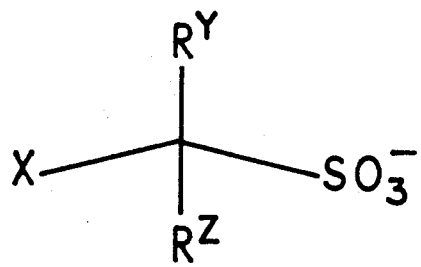
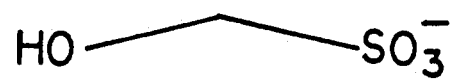
Fig. 1A            Fig. 1B
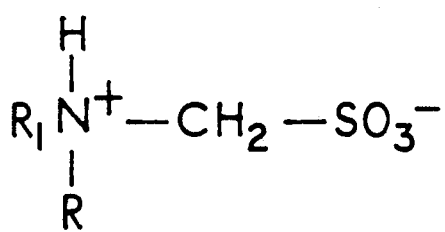
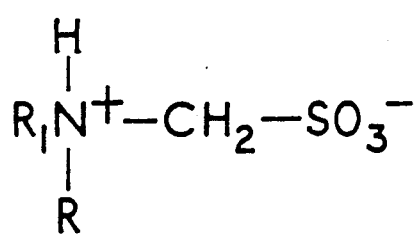
$R_1, R = CH_3$            $R_1, R = H$
Fig. 2A            Fig. 2B $R_2, R_3 = CH_2SO_3^-$ $R_2 = H, R_3 = CH_2SO_3^-$ n=2 n=3

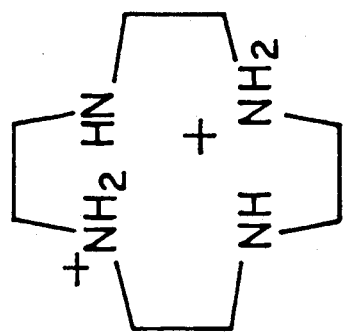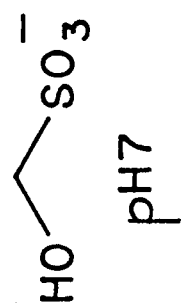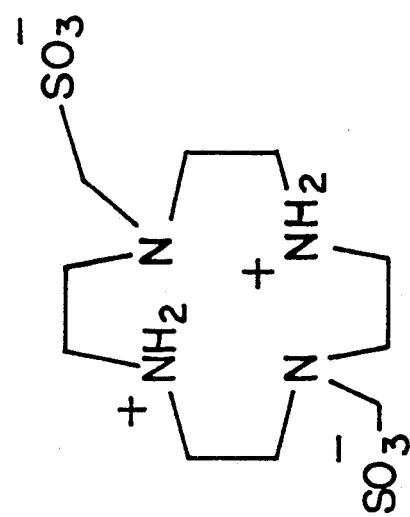
Fig. 15

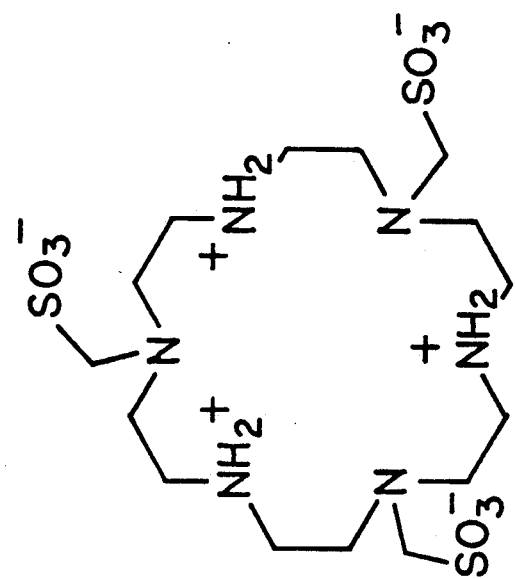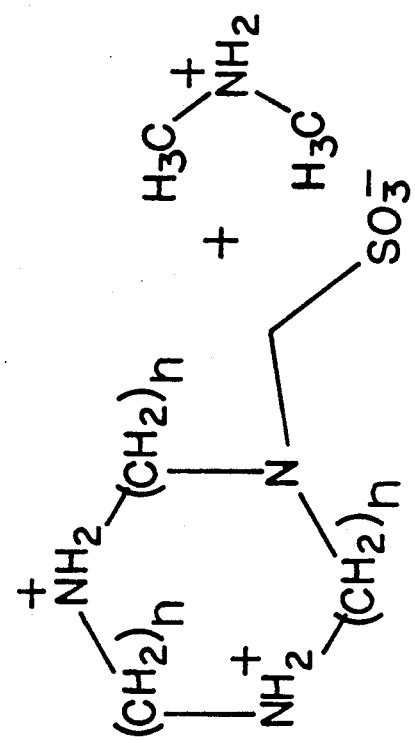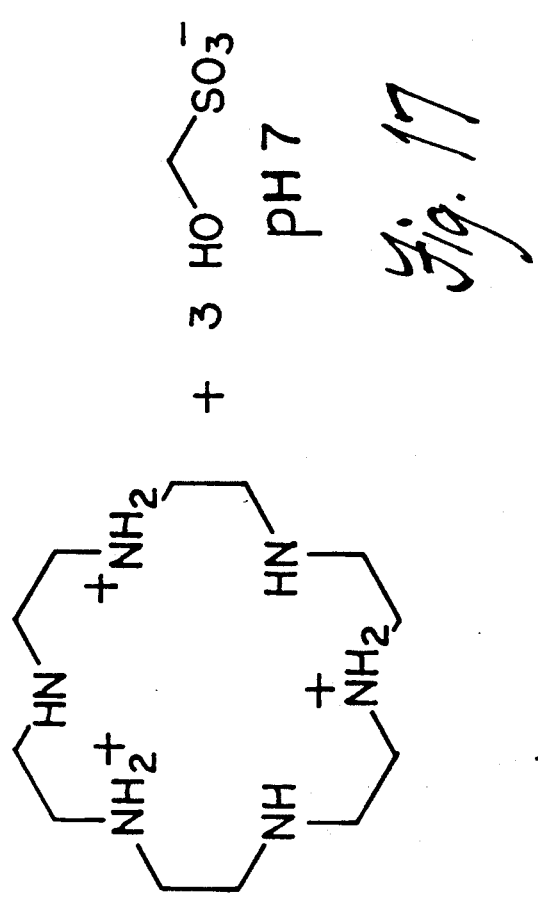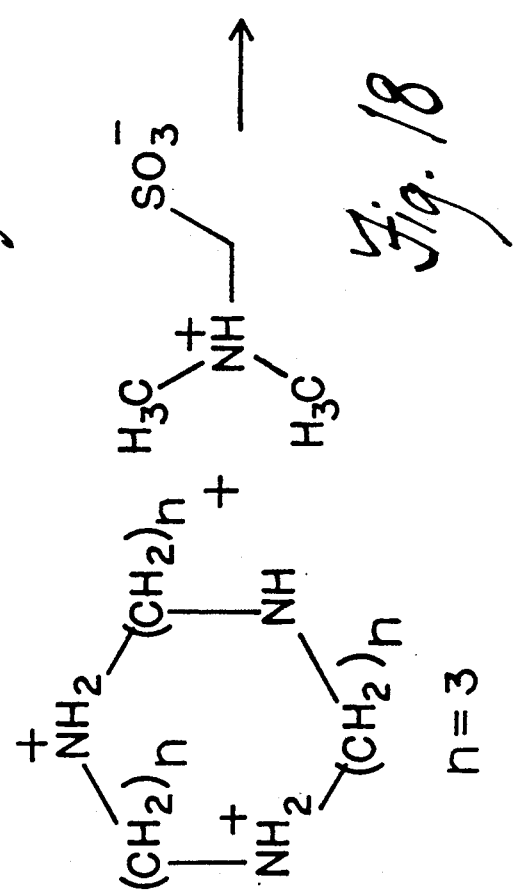
Fig. 17
Fig. 18

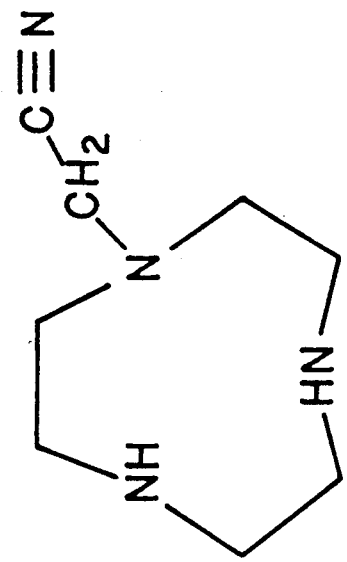
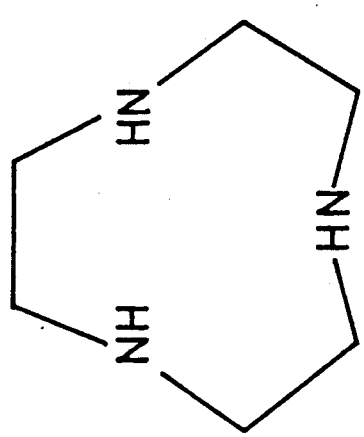
Fig. 20
Fig. 21

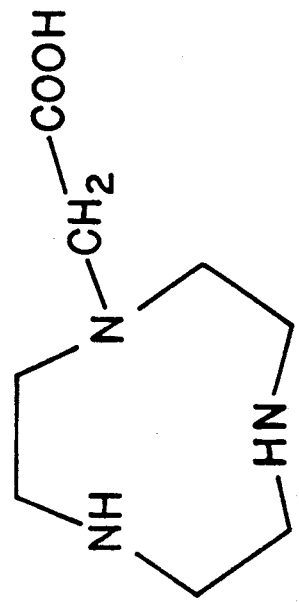
Fig. 23
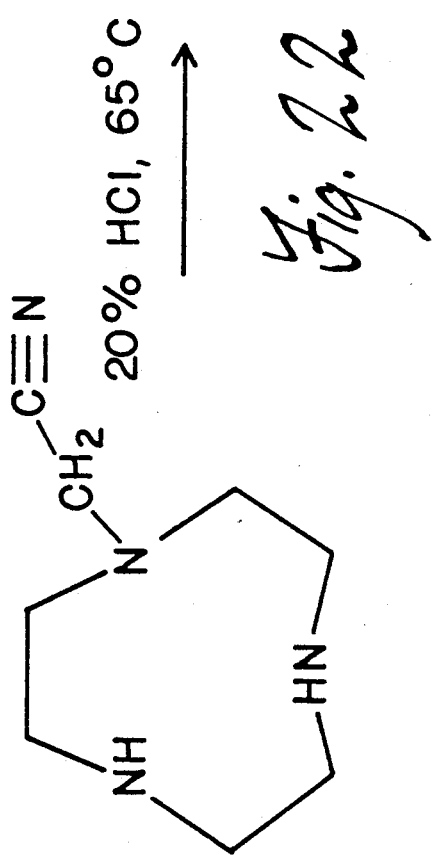
Fig. 22
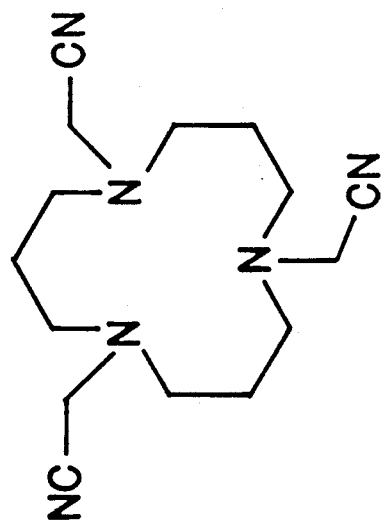

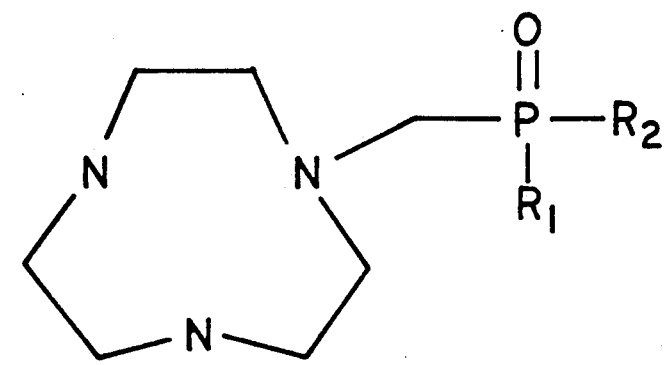
Fig. 3/A
$R_1, R_2 = OH: 21\%^d$
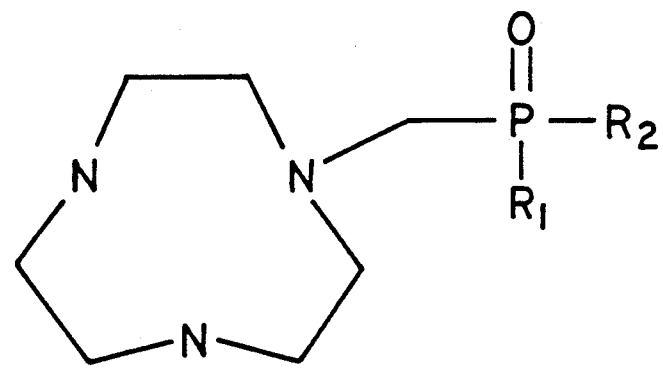
Fig. 3/B
$R_1 = OEt, R_2 = Et: 44\%^d$
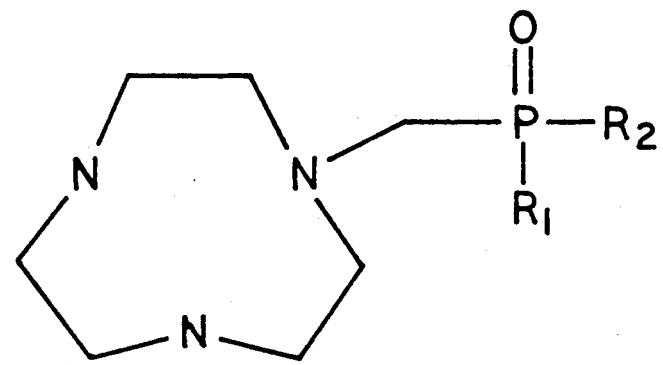
Fig. 3/C
$R_1, R_2 = OEt: 24\%^d$ $R_1, R_2 = OEt: 31\%^d$ $R_1 = OEt, R_2 = Et: 73\%^d$

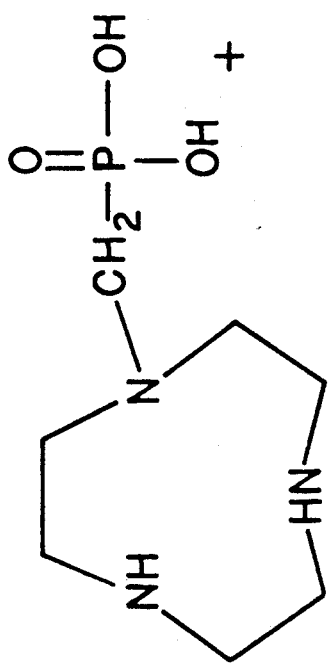
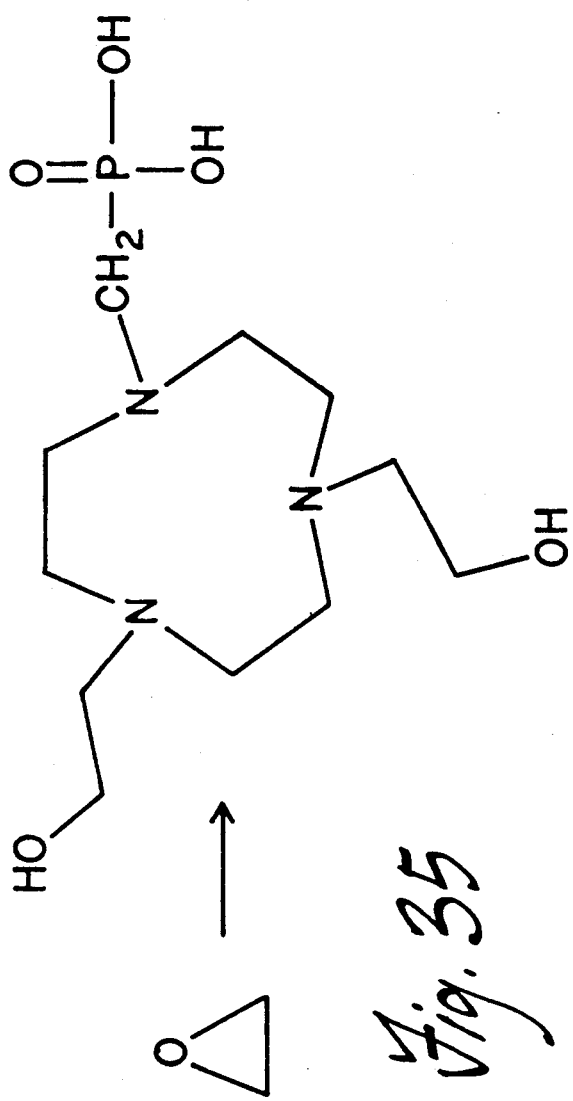
Fig. 35
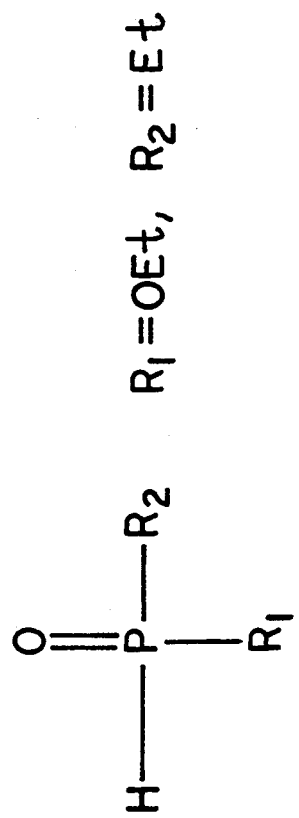
$R_1 = OEt, \quad R_2 = Et$
Fig. 36

SYNTHESIS OF POLYAZAMACROCYCLES WITH MORE THAN ONE TYPE OF SIDE-CHAIN CHELATING GROUPS

This is a continuation-in-part of U.S. Ser. No. 07/615,619 filed Nov. 19, 1990 pending, which is a continuation-in-part of U.S. Ser. No. 07/357,193 filed May 25, 1989 now abandoned and U.S. Ser. No. 07/291,053 filed Dec. 28, 1988 (now issued as U.S. Pat. No. 4,983,376), all of which are incorporated herein by reference. Application Ser. No. 07/291,053 was a continuation-in-part of application Ser. No. 007,729 filed Jan. 27, 1987 now abandoned, which was a continuation-in-part of application Ser. No. 662,075 filed Oct. 18, 1984 (now issued as U.S. Pat. No. 4,639,365).

BACKGROUND OF THE INVENTION

The high thermodynamic and kinetic stability of chelates formed between lanthanide(III) cations and polyazamacrocyclic ligands having pendent acetate (Desreux et al.; Stetter et al.; Hama et al.; Cortes et al.), phosphonate (Geraldes et al. (*Inorg. Chem.*); Polikarpou et al.; Delgado et al.), phosphonate monoester, and phosphinate side-chains have lead to considerable interest in their use as NMR shift reagents in biological systems or as magnetic resonance imaging (MRI) contrast agents (Lauffer). A new application for the tri- and tetraaza macrocycle derivatives having phosphorous-containing pendent groups is for noninvasive in vivo monitoring of intracellular concentrations of free Ca(II), Mg(II), and Zn(II) by $^{31}$P NMR (Ramasamy et al.).

In most cases, this application will require fine tuning of the binding constant under physiological conditions for a particular metal ion, keeping it in the same range as the free metal ion concentration in the cell, to achieve the desired equal concentrations of free ligand and metal ion complex.

One method of fine tuning is to introduce two or more different pendent groups onto the macrocycle, but the synthesis of polyazamacrocycles with specific numbers of even a single pendent N-substituent group (acetic acid, for example) has proven difficult with prior art methods (Neves et al.; Tweedle et al.; Kruper; Dischino et al; Studer et al.). Yields of diacetic acid derivatives prepared as in the prior art, with specified pendent group distributions, have been poor. Such conventional synthetic methods produce mixtures of the desired product with macrocycles having different pendent group distributions, thus necessitating subsequent separation of the desired species.

SUMMARY OF THE INVENTION

The present invention relates generally to chemical synthetic methods and compounds and complexes derived therefrom. In particular, methods of the present invention improve the yield of polyazamacrocyclic ligands having selected distributions of pendent N-substituted carboxylate, alkyl carboxylate, alkyl alcohol, alkyl ester, alkyl amide, alkyl phosphonate, alkyl phosphonate monoester, and alkyl phosphinate side-chains, as well as other nitrogen substituents.

More particularly, for example, selective (less than total) N-sulfomethylation is employed to prepare nearly quantitative amounts of disubstituted and trisubstituted methylenesulfonate derivatives of tetraaza- and hexaazamacrocycles respectively. High yields are obtainable during selective sulfomethylation because of the macrocycle protonation patterns which result from the close proximity of the ring nitrogens (Desreux et al.; Geraldes et al. (*Chem. Soc.*); Geraleds et al. (*Inorg. Chem.*); Kimura et al.; Zompa (1978); Yang; Zompa (1976), together with the surprisingly selective nature of the methylenesulfonate substituent.

Following sulfomethylation, the macrocycles' pendent sulfonate groups are replaced as desired by carboxylate, alkyl carboxylate, alkyl alcohol, alkyl ester, alkyl amide, alkyl phosphonate, alkyl phosphonate monoester, or alkl phosphinate groups to yield the desired geometric isomeric products.

Side chains and groups can be added to pendent methylene carbons as well as nitrogens not previously substituted to further tailor products to specific (in vivo) uses as MRI contrast agents or NMR shift reagents. For example, substitution of alkyl, aryl, alkyl acid, alkyl ether, alkyl ester, or alkyl alcohol groups on pendent methylene carbons, or substitution of chelating groups on otherwise unsubstituted ring nitrogens can alter chelating properties as well as water and lipid solubility. Such alterations may affect distribution of the macrocycle within the body as well as the charge and binding constant of complexes formed with paramagnetic ions.

One particular aspect of the invention relates to effective synthetic use of specific substitution reagents to take advantage of the unique protonation pattern of each macrocycle. For polyazamacrocycles with an even number of nitrogens, such as tetraazacyclododecane ([12]aneN4) and hexaazacyclooctadecane ([18]aneN6), a sharp division in $pK_a$'s is shown on half protonation (Table I). Prior synthetic schemes took no advantage of these $pK_a$ differences, but the present invention incorporates particular reagents containing a methylenesulfonate group to permit selective substitution on nitrogens of macrocycles having an adequate range of $pK_a$ values.

Specifically, the preferred substitution reagent for the present invention has a formula $X-CR^yR^zSO_3^-$, where X is a leaving group subject to displacement by a non-protonated nitrogen of the tetraazamacrocycle, and wherein $R^y$ and $R^z$ are independently hydrogen, alkyl, aryl, alkyl acid, alkyl ether, alkyl ester, or alkyl alcohol. The fact that the leaving group X is subject to displacement only by non-protonated nitrogen but not by protonated nitrogen is unexpected and important. Together with the range of $pK_a$'s found among the nitrogens of polyazamacrocycles, it is a basis for the selectivity of substitution which makes the present invention uniquely useful in synthetic chemistry.

The Examples describe experimental work on di-, tri-, tetra-, and hexaazamacrocycles, but those skilled in the art will recognize that other polyazamacrocycle configurations will exhibit analogous divisions of $pK_a$'s on partial protonation of the ring nitrogens. Such divisions mean that with careful selection of a reaction pH and a substitution reagent whose leaving group is subject to displacement by substantially nonprotonated nitrogens, selective substitutions may be made on a wide variety of polyazamacrocycles.

The product yield of such reactions will depend in part on the reaction pH, which controls the distribution of substantially (>50%) protonated and substantially (<50%) nonprotonated nitrogens, the desired substitutions occurring on the latter nitrogens. Wider separation between $pK_a$'s of protonated and nonprotonated nitrogens results a wider range of acceptable reaction pH's between the lowest $pK_a$ of nitrogens to be protonated but not substituted, and the highest $pK_a$ of nitrogens to be non-protonated and therefore selectively substituted. Wider separation of $pK_a$'s of interest also implies greater specificity in the sulfomethylation reaction.

Such separations may be exploited wherever found if application of the present invention would result in a greater efficiency than that obtainable by conventional methods of chemical synthesis. The choice of methods would depend on considerations such as cost of reagents and the difficulty of separating desired product from a mixture of other products.

For example, triazamacrocycles may be monosubstituted by a conventional approach employing a relative excess of the triazamacrocycle over the substitution reagent. But sulfomethylation of [9]aneN3 or [12]aneN3 at a pH of about 4 also produces monosulfomethylated derivatives in high yields. Dimethylaminomethylenesulfonic acid (FIG. 2A) is the preferable sulfomethylating agent at this pH because it exchanges a dimethylamino group only for the available nonprotonated amines in [9]aneN3 or [12]aneN3, thus providing an elegant synthetic route to the monosulfomethylated analogs. If a derivative of methylenesulfonate is the substituent desired, the present invention could result in higher yields and purer products, whereas the conventional approach could be simpler.

For this reason, preferred embodiments of the present invention emphasize preparation of compounds which are relatively difficult or uneconomic to prepare by conventional methods. Given that constraint, selective sulfomethylation of di-, tri-, tetra-, and hexaazamacrocycles may be carried out successfully over a wide pH range (3–11) using reagents which comprise a methylenesulfonate group with a leaving group on the methylene carbon. Preferred leaving groups include dimethylamino and hydroxyl, although others with appropriate stability at the selected reaction pH may be used. This structure takes advantage of relatively low avidity in the methylenesulfonate group when the leaving group is displaced, allowing the targeting of nitrogens with a particular range of $pK_a$ values for substitution.

Such selectivity in the substitution reagents of the present invention contrasts with that of conventional substitution reagents such as chloroacetic acid. In the latter case, the acetic acid group remaining after displacement of chlorine is so reactive that it will substitute on all four nitrogen atoms of [12]andN4 at pH 7. On the other hand, using the present invention in the context of the sharp division of $pK_a$'s for [12]aneN4 macrocycles results in selective symmetrical disulfomethylation at neutral pH; a single disubstituted [12]aneN4 is produced in high yield. Similar considerations apply to [18]aneN6, wherein under similar conditions a single trisubstituted [18]aneN6 is preferentially formed.

Further, of the two possible regioisomers of the disulfomethylated [12]aneN4, the 1,7-regioisomer is formed with a high degree of specificity (9:1) (the crystalization in ethanol/water gives the 1,4,7,10-tetraazacyclododecane-N,N'' dimethane sulfonate in pure form), as confirmed by X-ray crystallography and $^{13}C$ NMR. The comparable product of trisulfomethylated [18]aneN6 is symmetrically substituted on alternate nitrogens of the ring.

Those skilled in the art will recognize that groups with self-stabilizing characteristics similar to those of methylenesulfonate could serve a similar function in substitution reagents for tetra-, penta-, septa- and hexaazamacrocycles and related compounds having both more and fewer nitrogens.

Putative alternate substitution reagents should be evaluated as those comprising methylenesulfonate have been to insure analogous performance in the methods of the present invention. For example, the X-ray structures of piperazinylmethylenesulfonic acid, sodium hydrogen 1,4,7-triazacyclononane-N,N'-bis(methylenesulfonate), and 1,4,7,10-tetraazacyclododecane-N,N'''-bis(methylenesulfonic acid) show that sulfamides are not formed under these reaction conditions, and that the unsubstituted nitrogens are indeed protonated. Such protonation inhibits the sulfomethylation reaction and explains the selective nature of substitution using the present invention.

Following sulfomethylation, one may oxidatively hydrolyze the sulfomethyl groups on piperazines, monosulfomethylated [9]aneN3, and to a lesser extent, monosulfomethylated [12]aneN3 using triiodide. In fact, monosulfomethylated [9]aneN3 and [12]aneN3 react so slowly with triiodide that these compounds may be isolated as stable triiodide salts.

BRIEF DESCRIPTION OF THE DRAWINGS

FIG. 1A. Formula for the preferred substitution reagent, where X is a leaving group subject to displacement by a non-protonated nitrogen of a polyazamacrocycle and where $R^y$ and $R^z$ are independently hydrogen, alkyl, aryl, alkyl acid, alkyl ether, alkyl ester, or alkyl alcohol.

FIG. 1B. Hydroxymethylsulfonate, the adduct formed by formaldehyde and sodium bisulfite.

FIG. 2A. Dimethylaminomethylenesulfonic acid.

FIG. 2B. Aminomethylenesulfonic acid.

FIG. 15. Sulfomethylation of the tetraazamacrocycle [12]aneN4 at pH 7 yields the disulfomethylated product exclusively.

FIG. 17. Reaction of [18]aneN6 with 3 moles of formaldehyde sodium bisulfite at pH 7 gives the 1,7,13-trisubstituted derivative 1,4,7,10,13,16-hexaazacyclooctadecane-N,N'',N''''-tris(methylenesulfonate) as the main product.

FIG. 18. Equimolar amounts of dimethylaminomethylenesulfonic acid and [12]aneN3 at pH 3.5 give complete conversion to 1,5,9-triazacyclododecane-N-methylenesulfonate hydrotriiodide, plus the dimethylammonium ion after 16 hours at 25° C., as indicated by NMR.

FIG. 20. The conversion of an aminomethylenesulfonate to an amino acid via nucleophilic substitution of cyanide for sulfonate.

FIG. 21. Formation of N-cyanomethyl-1,4,7-triazacyclononane in the same reaction mixture after formation of monosulfomethylated [9]aneN3 at pH 4.

FIG. 22. Acidic hydrolysis of N-cyanomethyl-1,4,7-triazacyclononane with 20% HCl at 65° C. for 24 hours to form triazacyclononane-monoacetic acid.

FIG. 23. The tricyanomethylated derivative of [12]aneN3.

FIGS. 31A, 31B, and 31C. The monomethylenephosphonate (31A), the monomethylene(ethyl)phosphinate ethyl ester (31B) and the monomethylenephosphonate diethyl ester (31C) of [9]aneN3.

FIG. 34. The monomethylene(ethyl)-phosphinate ethyl ester of [9]aneN3 is hydrolyzed to yield 1,4,7-triazacyclononane-N-(methylene-ethylphosphinic) acid as an intermediate, and that product is purified by cation exchange column prior to its reaction with chloroacetic acid to yield 1,4,7-triazacyclononane-N-methylene-ethylphosphinic acid)-N',N''-diacetic acid.

FIG. 35. The monomethylenephosphonate-di(hydroxyethyl) derivative of 1,4,7-triazacyclononane, prepared with a yield of 45% by reaction of oxirane with 1,4,7-triazacyclononane-N-methylenephosphonic acid.

FIG. 36. Ethylmonoethylphosphonite.

DESCRIPTION OF THE PREFERRED EMBODIMENTS

Figure 3A:
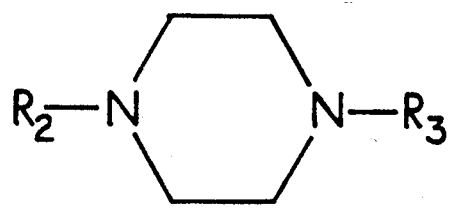
FIG. 3A. Disodium piperazine-N,N'-bis(methylenesulfonate).

The present invention is directed toward polyazamacrocyclic ligands and metal complexes thereof useful as NMR shift reagents or MRI contrast agents, as well as methods of producing such ligands. Specific preferred embodiments of the invention have structures and synthetic methods which depend on the desired end use and the metal ions to be chelated. Preferred for MRI contrast agents are the paramagnetic lanthanide metals—especially gadolinium. Preferred for NMR shift agents are the paramagnetic lanthanide metals—with the exception of gadolinium. Synthetic methods of the present invention all comprise a process wherein selective (less than total) N-sulfomethylation is carried out on a precursor polyazamacrocycle of the form

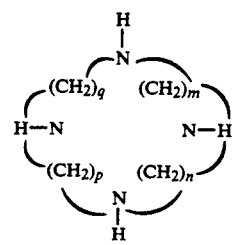

for tetraazamacrocycles, and of the form

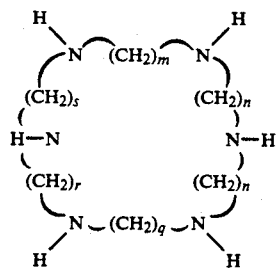

for hexaazamacrocycles.

Selective sulfomethylation produces selectively N-substituted pendent methylenesulfonate groups. For tetraazamacrocycles, the resulting N-substituted compounds have the formula

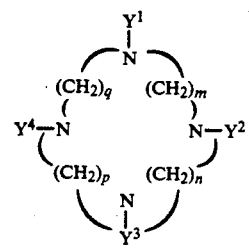

whereas for hexaazamacrocycles, the corresponding formula is

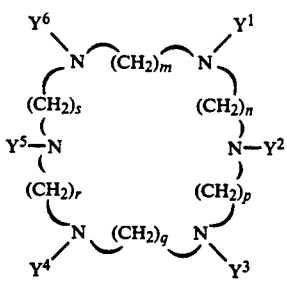

A first scheme for selective sulfomethylation may be carried out by obtaining $pK_a$'s for nitrogens of the precursor polyazamacrocycle and reacting, in an aqueous solution having a pH between the lowest $pK_a$ of nitrogens to be protonated but not substituted, and the highest $pK_a$ of nitrogens to be non-protonated and selectively substituted, the precursor polyazamacrocycle with a substitution reagent to produce, for example, a tetra- or hexaazamacrocycle with selectively substituted pendent methylenesulfonate groups.

A second scheme for selective N-sulfomethylation of a precursor polyazamacrocycle comprises estimation or assumption of the $pK_a$'s of macrocycle nitrogens, followed by reacting, in an aqueous solution having a pH between a lowest $pK_a$ of nitrogens to be protonated but not substituted, and a highest $pK_a$ of nitrogens to be non-protonated and selectively substituted, the precursor polyazamacrocycle with a substitution reagent as described above to produce compounds similar to the product of the first scheme.

A third scheme for selective N-sulfomethylation of a precursor polyazamacrocycle comprises reacting the above substitution reagent with a precursor polyazamacrocycle having at least one nitrogen substantially protonated and at least one nitrogen substantially nonprotonated and selectively substituted to produce, again, a tetra- or hexaazamacrocycle with selectively substituted pendent methylenesulfonate groups.

Protonated nitrogens in the foregoing schemes have a positive charge, whereas nonprotonated nitrogens carry no charge. Additionally, in each of the above three approaches, the substitution reagent has a formula $X\text{-}CR^yR^zSO_3^-$, where X is a leaving group (for example, dimethylamino or hydroxyl) subject to displacement by a non-protonated nitrogen of the precursor polyazamacrocycle and where $R^y$ and $R^z$ are independently hydrogen, alkyl, aryl, alkyl acid, alkyl ether, alkyl ester, or alkyl alcohol. Specific substitution reagents may be ordered from commercial sources or synthesized by mixing sodium bisulfites or other bisulfite salts and a variety of aldehydes, ketones, ketoacids, etc.

Preferred embodiments of the present invention comprise selective N-sulfomethylation of 1,4,7,10-tetraazacyclododecane or 1,4,7,10,13,16-hexaazacyclooctadecane at a pH of about 7 with a substitution reagent which is an adduct of formaldehyde and sodium bisulfite, yielding predominantly the disubstituted and trisubstituted products from the tetraaza- and hexaaza-precursor macrocycles respectively. Both the disubstituted and trisubstituted products are symmetrically substituted, meaning in the context of this specification that every other nitrogen around the macrocycle ring is substituted.

Other preferred embodiments of the present invention comprise mono-N-sulfomethylation of 1,4,7,10-tetraazacyclododecane or 1,4,7,10,13,16-hexaazacyclooc-
tadecane at a pH of about 3.5 with a substitution reagent comprising dimethylaminomethylenesulfonic acid.

Still other examples of preferred embodiments would be an MRI contrast agent comprising a complex of a paramagnetic lanthanide (III) cation (such as gadolinium (III)) with a ligand, or an NMR shift reagent with a bound paramagnetic lanthanide cation excluding gadolinium. In either case, the ligand would have the formula 1,4,7,10-tetraazacyclododecane-(N,N'''-diacetic acid)-(N'-$R^1$)-(N''''-$R^2$) or 1,4,7,10,13,16-hexaazacyclooctadecane-(N,N'',N''''-triacetic acid)-(N'-$R^1$)-(N'''-$R^2$)-(N'''''-$R^3$), where $R^1$, $R^2$ and $R^3$ are independently selected from the group consisting of:

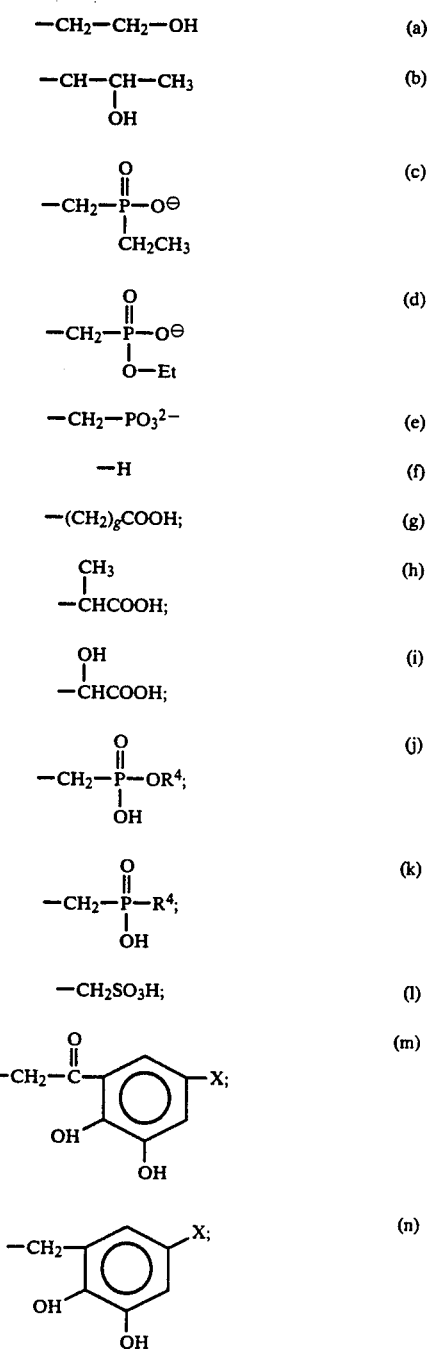

-continued

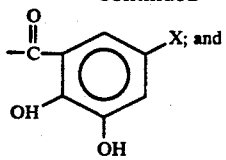

where $R^4$ is $-C_qH_{2q+1}$; X is selected from the group consisting of $-SO_3H$, $-COOH$, and salts thereof; and q is 1-10.

In addition to the above substitutions for $R^1$, $R^2$ and $R^3$ in 1,4,7,10-tetraazacyclododecane-(N,N''-diacetic acid)-(N'-$R^1$)-(N'''-$R^2$) or 1,4,7,10,13,16-hexaazacyclooctadecane-(N,N'', N''''-triacetic acid)-(N'-$R^1$)-(N'''-$R^2$)-(N'''''-$R^3$), the present invention also comprises these two families of compounds wherein $R^1$, $R^2$ and $R^3$ are all hydrogen and at least one of the acetic acid groups is replaced by another alkyl carboxylate, an alkyl alcohol, an alkyl ester or an alkyl amide. Compounds formed by subsequent replacement of $R^1$, $R^2$ and $R^3$ independently by one or more of the above substituents (a) through (o) are also included within the present invention.

Similarly, the sulfonate groups of 1,4,7,10-tetraazacyclododecane-(N,N''-bis(methylenesulfonate))-(N'-$R^1$)-(N'''-$R^2$) or 1,4,7,10,13,16-hexaazacyclooctadecane-(N,N'',N''''-tris(methylenesulfonate))-(N'-$R^1$)-(N'''-$R^2$)-(N'''''-$R^3$), where $R^1$, $R^2$ and $R^3$ are hydrogen, may be replaced by phosphonate, phosphonate monoester, or phosphinate groups, followed by $R^1$, $R^2$ and $R^3$ substitutions as described above.

The invention thus comprises a variety of compounds, methods and uses characterized by relatively high synthetic yields of ligands exhibiting a wide and predictable choice of metal ion binding constants, a choice of charges on the ligand-ion complex, and a choice of lipid/water solubility characteristics.

Those skilled in the art will recognize that substantial alterations in macrocycle structure, pendent group structure and variety, or ion(s) chelated, as well as the order and number of synthetic steps, are included as embodiments and aspects of the present invention.

TABLE I

| Protonation constants of amines (25° C.) | | | | |
|---|---|---|---|---|
| Amine | log $K_1$ | log $K_2$ | log $K_3$ | log $K_4$ |
| $(CH_3)_2NH$ | 10.77 | | | |
| piperazine | 9.83 | 5.56 | | |
| [9]aneN3[a] | 10.42 | 6.82 | low[b] | |
| [12]aneN3[a] | 12.60 | 7.57 | 2.41 | |
| [12]aneN4 | 10.6[c] | 9.6[c] | 1.5[d] | 0.7[d] |
| [18]aneN6e | 10.07 | 9.11 | 8.61 | 3.97 |

[a]0.1M $KNO_3$ (Gilbert)
[b]Not determined
[c]0.1M $NaClO_4$ (Smith & Martel)
[d]35° C., 0.2M $NaClO_4$
[e]0.M $NaClO_4$ (Kimura et al.; Smith & Martel)

EXAMPLES

The following examples are presented to describe preferred embodiments and utilities of the present invention and are not meant to limit the invention unless otherwise stated in the claims appended hereto. Taken together, the examples illustrate representative demonstrations of the best mode of implementing the invention as currently understood.

EXAMPLE 1

Preparation of Methylenesulfonate Derivatives

General—The macrocycles 1,4,7-triazacyclononane ([9]aneN3), 1,5,9-triazacyclododecane ([12]aneN3), [12]aneN3.3HBr, and 1,4,7,10,13,16-hexaazacyclooctadecane.3$H_2SO_4$ ([18]aneN6), the formaldehyde sodium bisulfite addition compound (FIG. 1), and aminomethylenesulfonic acid (FIG. 2B) are obtainable from Aldrich. 1,4,7,10-tetraazacyclododecane.4 HCl ([12]aneN4) is obtainable from Parish Chemical Company. Dimethylaminomethylenesulfonic acid (FIG. 2A) is prepared in 40% yield with a 92% purity (iodometric assay) according to a modified Backer and Mulder procedure(Backer et al., 1933). The NMR spectra are recorded on a JEOL JNM-FX200; the methyl group of t-butanol is used as an internal reference at 1.2 ppm ($^1H$ NMR) or at 31.2 ppm ($^{13}C$ NMR). Elemental analyses are performed by ONEIDA Research Service, Inc., New York.

Disodium piperazine-N,N'-bis(methylenesulfonate), FIG. 3A. An aqueous solution (5 mL) containing piperazine (10 mmol, 0.86 g) and $HOCH_2SO_3Na$ (20 mmol, 2.68 g) is heated for 2 hours at 70° C. The precipitate which forms is filtered off and washed with ethanol (10 mL) and ether (10 mL). The product is obtained in 51% yield (1.79 g). $^1H$ NMR ($D_2O$): 3.81 (s,4H), 2.91 (s, 8H); $^{13}C$ NMR ($D_2O$): 73.0, 51.5. Anal. Calcd. for $C_6H_{12}N_2S_2O_6Na_2$.2 $H_2O$: C, 20.34; H, 4.55; N, 7.91; S, 18.10. Actual: C, 20.34; H, 4.54, 7.82; S, 18.22.

Figure 3B:
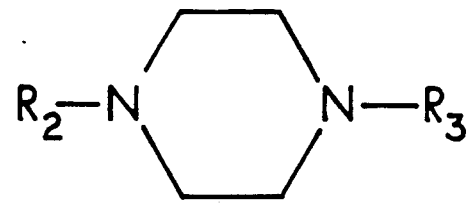
FIG. 3B. Piperazinylmethylenesulfonic acid.

Piperazinylmethylenesulfonic acid, FIG. 3B. An aqueous solution (3 ml) containing piperazine (2 mmol, 0.172 g) neutralized with hydrochloric acid (2 mmol) and $HOCH_2SO_3Na$ (2.1 mmol, 0.282 g) is heated for 2 hours at 40° C. Ethanol (10 ml) is added to the solution and after a few hours a white product crystallizes. The crystals are suitable for X-ray diffraction. Yield 51% (1.02 mmol, 0.188 g). $^1H$ NMR ($D_2O$): 3.82 (s, 2H), 3.24 (m, 4H), 3.12 (m, 4H); $^{13}C$ NMR ($H_2O$)/$D_2O$): 72.95, 49.14, 44.27. Anal. Calcd. for $C_5H_{12}N_2SO_3$.0.25 $H_2O$: C, 32.51; H, 6.77; N, 15.16; S, 17.36. Actual: C, 32.63; H, 6.59; N, 15.25; S, 19.03.

Figure 4:
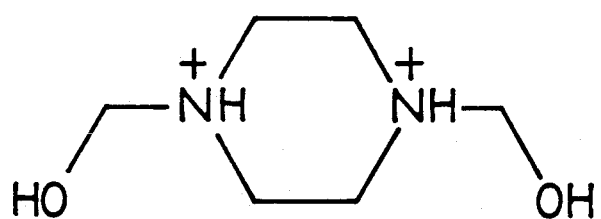
FIG. 4. Piperazine-N,N'-bis(hydroxymethylene) sodium hydrogen sulfate.

Piperazine-N,N'-bis(hydroxymethylene) sodium hydrogen sulfate, FIG. 4. Iodine (2.09 mmol, 0.530 g) and sodium iodide (2.00 mmol, 0.30 g) are dissolved in 4 mL of water. The iodine that does not dissolve is filtered off prior to the addition of disodium piperazine-N,N'-dimethylenesulfonate (FIG. 3A) (1.01 mmol, 0.322 g). Two minutes after the addition, the solution turns clear and a white precipitate forms. The crystals are filtered and washed with ethanol and ether. Yield 34% (0.111 g). IR (cm−1): 3459, 3421 (O—H), 3026, 2970 (C—H), 2534–2342 (N+—H), 1629, 1463 (C—N). Anal. Calcd. for $C_6H_{14}N_2O_2$.$NaHSO_4$.0.25 $NaI.H_2O$: C, 22.40; H, 5.32; N, 8.71; I, 9.86. Actual: C, 22.50; H, 5.22; N, 9.10; I, 9.67. $^1H$ NMR ($D_2O$) after heating at 80° C.: 4.02 (s, 2H), 3.39 (s, 4H). Decomposition to piperazinylmethanol: 4.11 (s, 2H), 3.55 (s, 4H), 3.42 (s, 4H) and dihydroxymethylene 4.35 (s) occurs.

Figure 5A:
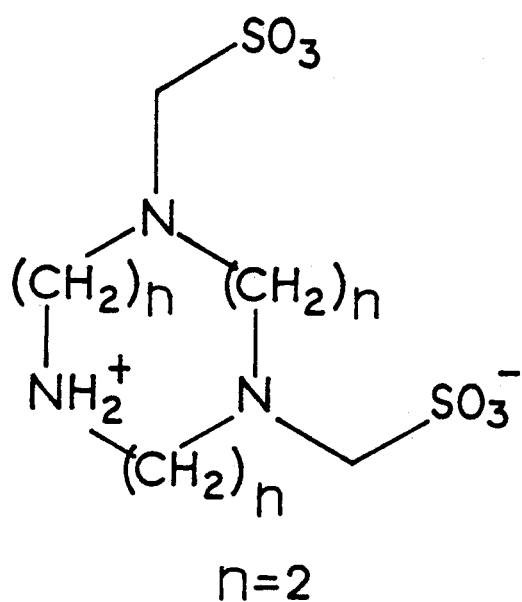
FIG. 5A. Hydrogen sodium 1,4,7-triazacyclononane-N,N'-bis(methylenesulfonate).

Hydrogen sodium 1,4,7-triazacyclononane-N,N'-bis(methylenesulfonate), FIG. 5A. [9]aneN3.3 HCl (1 mmol, 0.239 g) is dissolved in water (3 mL), is neutralized with NaOH (1.342 mL, 1.49M), and mixed with $HOCH_2SO_3Na$ (2.1 mmol, 0.282 g). The final solution pH is 9.5. The reaction is complete after heating for 16 hours at 40° C. Ethanol (10 mL) is added and the product slowly crystallizes. The crystals are filtered and washed with ethanol and ether. Yield 97% (0.373 g). Recrystallization in 50/50 water/ethanol gives crystals that are suitable for X-ray diffraction. $^1$H NMR (D$_2$O): 3.98 (s, 4H), 3.17 (s, 8H), 3.01 (s, 4H). $^{13}$C NMR (D$_2$O/H$_2$O): 73.58, 51.76, 49.36, 46.07. Anal. Calcd. for C$_8$H$_{18}$N$_3$S$_2$O$_6$Na.2.5 H$_2$O: C, 25.00; H, 6.03; N, 10.93; S, 16.68. Actual: C, 24.81; H, 5.78; N, 10.85; S, 17.45.

Figure 5B:
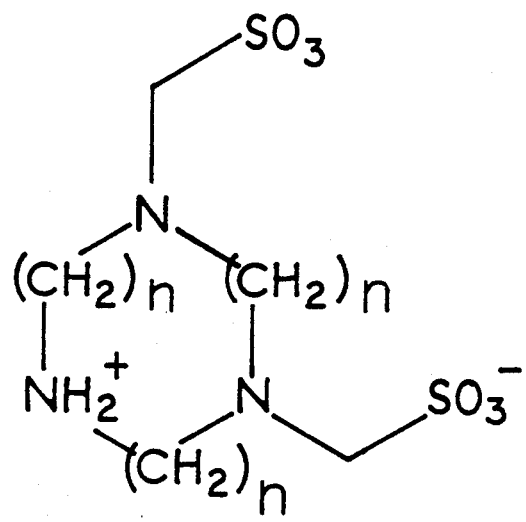
FIG. 5B. Disodium 1,5,9-triazacyclododecane-N,N''-bis(methylenesulfonate) hydrochloride.

Disodium 1,5,9-triazacyclododecane-N,N''-bis(methylenesulfonate) hydrochloride, FIG. 5B. [12]aneN3 (1.206 mmol 0.206 g) is dissolved in water (3 mL), neutralized with HCl (1.047 mL, 1.152M), and mixed with HOCH$_2$SO$_3$Na (2.533 mmol, 0.340 g). The final solution pH is 6.9. The reaction is complete after 16 hours at 40° C. Ethanol is added and the solution is evaporated in vacuo at 40° C. The resulting precipitate is treated with acetone (50 mL), filtered and washed with ether. Yield 98% (0.540 g). $^1$H NMR (D$_2$O): 3.74 (s, 4H), 3.13, 3.03, 2.78 (bs, 4H), 1.88 (bs, 6H). $^{13}$C NMR (D$_2$O/H$_2$O): 69.0, 55.48, 48.40, 47.58, 23.20, 22.40. Anal. Calcd. for C$_{11}$H$_{23}$N$_3$S$_2$O$_6$Na$_2$.H$_2$O: C, 28.85; H, 5.72; N, 9.18; S, 14.00. Actual: C, 28.83; H, 5.49; N, 8.25; S, 13.89.

Figure 6:
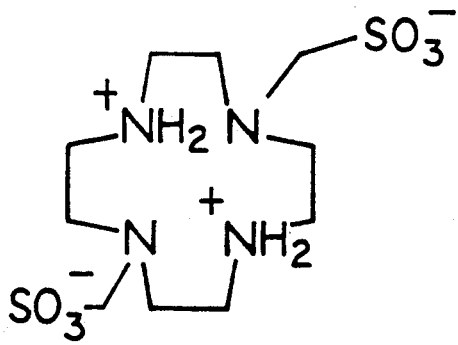
FIG. 6. 1,4,7,10-tetraazacyclododecane-N,N''-bis(methylenesulfonic acid).

1,4,7,10-tetraazacyclododecane-N,N''-bis(methylenesulfonic acid), FIG. 6. [12]aneN4.4 HCl (1 mmol, 0.318 g) is dissolved in water (3 mL), neutralized with NaOH (1.342 mL, 1.49M), and mixed with HOCH$_2$SO$_3$Na (2.1 mmol, 0.282 g). The final pH of the mixture is 7. After heating for 16 hours at 40° C. the reaction is complete. Ethanol (10 mL) is added and the reaction mixture is evaporated. Addition of fresh ethanol gives an oil that slowly crystallizes. The crystals are filtered and washed with ethanol and ether. Yield 95% (0.565 g). Sodium chloride is present in the solid as well. The ratio of 1,7-disubstituted: 1,4-disubstituted is 9:1. The product is further purified by fractional recrystallization in ethanol/water. NaCl crystallizes first. After adding extra ethanol to the reaction mixture, large needle shaped crystals of pure 1,7-disubstituted product form; they are suitable for X-ray diffraction. $^1$H NMR (D$_2$O): 3.83 (s, 4H), 3.12 (s, 16H). $^{13}$C NMR (D$_2$O/H$_2$O): 71.61, 51.56, 45.67. Anal. Calcd. for C$_{10}$H$_{24}$N$_4$S$_2$O$_6$·2 H$_2$O: C, 30.29; H, 7.12; N, 14.13; Actual: C, 30.25; H, 7.05; N, 13.98.

Figure 7:
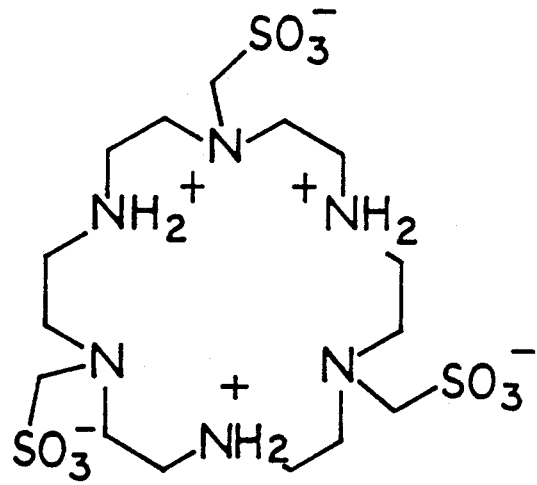
FIG. 7. 1,4,7,10,13,16-hexaazacyclooctadecane-N,N'',N''''-tris(methylenesulfonate).

1,4,7,10,13,16-hexaazacyclooctadecane-N,N''',N''''-tris(methylenesulfonate), FIG. 7. [18]aneN6.3 H$_2$SO$_4$ (1 mmol, 0.556 g) is dissolved in water (10 mL) and neutralized with NaOH (2.105 mL, 1.424M). HOCH$_2$SO$_3$Na (7.53 mmol, 1.01 g) and Na$_2$HPO$_4$/KH$_2$PO$_4$ (pH 7 buffer: pHydrion dry, 4.85 g) is added. The mixture is heated for 3 days, during which time a product crystallizes from solution. The product is filtered off and washed with ethanol (50 mL) and ether (50 mL). Yield 52.5% (0.284 g). $^1$H NMR (D$_2$O): 3.93 (s, 6H), 3.30 (bs, 12H), 3.18 (bs, 12H). $^{13}$C NMR (D$_2$O): 69.83, 53.20, 47.64. Anal. Calcd. for C$_{15}$H$_{36}$N$_6$S$_3$O$_{13}$K$_3$.H$_3$PO$_4$.1.5 H$_2$O: C, 23.10; H, 5.06; N, 10.81; S, 12.37. Actual: C, 23.24; H, 5.28; N, 10.66; S, 12.30. $^{31}$P NMR (H$_2$O, pH 7, ref. 85% H$_3$PO$_4$/H$_2$O): 1.66.

Figure 8A:
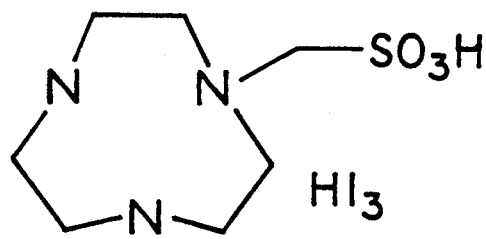
FIG. 8A. 1,4,7-triazacyclononane-N-methylenesulfonate hydrotriiodide.

1,4,7-triazacyclononane-N-methylenesulfonate hydrotriiodide, FIG. 8A. [9]aneN3 (8.79 mmol, 1.136 g) is dissolved in water (10 mL) and 17.6 mL of 1.0M HCl added followed by 1.84 g of (CH$_3$.)$_2$NCH$_2$SO$_3$H (FIG. 2A). The pH of the resulting mixture is 3.80. After 16 hours at 25° C. the reaction is complete. $^{13}$C NMR (D$_2$O/H$_2$O): 72.93, 50.93, 45.81, 44.10, 36.43 ((CH$_3$)$_2$NH$_2^+$). $^1$H NMR (D$_2$O: 4.026 (s, 2H), 3.689 (s, 2H), 3.347 (bs, 8H), 2.692 (s, 6H, (CH$_3$)$_2$NH$_2^+$). An aqueous solution (7 mL) containing iodine (13.21 mmol, 3.353 g) and sodium iodide (26.42 mmol, 3.96 g) is added to the reaction mixture. Almost immediately, a brown precipitate is formed. The precipitate is filtered off and washed with ethanol (50 mL) and ether (50 mL) yielding brown crystals, 93% yield (4.942 g). Anal. Calcd. for C$_7$H$_{18}$N$_3$SO$_3$I$_3$.0.5 H$_2$O: C, 13.69; H, 3.12; N, 6.84; S, 5.22. Actual: C, 13.69; H, 3.01; N, 6.70; S, 5.53. 1,4,7-triazacyclononane-N-methylenesulfonate.HI$_3$ can be reduced to the hydroiodide salt by diethylphosphite. The I$_3$ salt (0.11 mmol, 66.7 mg) is suspended in ethanol (0.5 mL) and HP(=O)(OEt)$_2$ (21.3 µl) is added. The brown solid completely decolorizes upon reaction. The precipitate is filtered off and washed with ether (10 mL). Yield 35.79 mg. This salt is now readily soluble in D$_2$O. $^1$H NMR (D$_2$O): 3.98 (s, 2H), 3.67 (s, 4H), 3.33, 3.29 (2*bs, 8H).

Figure 8B:
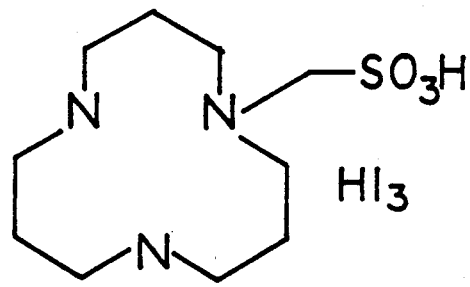
FIG. 8B. 1,5,9-triazacyclododecane-N-methylenesulfonate hydrotriiodide.

1,5,9-triazacyclododecane-N-methylenesulfonate hydrotriiodide, FIG. 8B. [12]aneN3.3 HBr (2.42 mmol, 1 g) is dissolved in water (4 mL) and neutralized with NaOH (1.696 mL, 1.424M). Dimethylaminomethylenesulfonic acid (0.5043 g) is added. The pH of the reaction mixture is 4.3. After 16 hours at room temperature the reaction is complete. $^{13}$C NMR (D$_2$O/H$_2$O): 70.78, 54.84, 46.23, 43.64, 23.27, 21.63. A (CH$_3$)$_2$NH$_2^+$ resonance is present at 36.43 ppm. An aqueous solution (2 mL) containing iodine (2.42 mmol, 0.61 g) and sodium iodide (4.83 mmol, 0.724 g) is added and the HI$_3$ salt is isolated as described for (FIG. 1). Yield 65% (1.0722 g). Anal. Calcd. for C$_{10}$H$_{24}$N$_3$SO$_3$I$_3$.H$_2$O: C, 18.06; H, 3.94; N, 6.32; S, 4.82. Actual: C, 18.01; H, 3.62; N, 6.33; S, 4.46.

EXAMPLE 2

Crystal Structure Determination

X-ray intensity data for structure shown in FIG. 3B FIG. 5A, and FIG. 6 were collected on an Enraf-Nonius CAD-4 diffractometer using an omega-2 theta scan technique. Relevant crystallographic data for the compounds are given in Table II.

TABLE II

| Summary of Crystallographic Data for FIGS. 3B, 5A and 6 | | | |
|---|---|---|---|
| | FIG. 3B | FIG. 5A | FIG. 6 |
| formula | C$_5$H$_{12}$N$_2$SO$_3$ | C$_8$H$_{22}$N$_3$S$_2$O$_8$Na | C$_{10}$H$_{28}$N$_4$S$_2$O$_8$ |
| formula weight | 180 | 375 | 404 |
| space group | C2/c | Pna2$_1$ | P2$_1$/n |
| | monoclinic | orthorhombic | monoclinic |
| a, Å | 17.528(1) | 17.963(1) | 9.154(1) |
| b, Å | 6.811(5) | 10.152(1) | 13.589(6) |
| c, Å | 13.912(6) | 8.269(3) | 14.020(1) |
| β, deg. | 108.21(8) | | 94.15(7) |
| V, Å$^3$ | 1578 | 1508 | 1739 |
| Z | 8 | 4 | 4 |
| d$_{calc}$, g/cm$^3$ | 1.52 | 1.65 | 1.54 |
| µ, cm$^{-1}$ | 3.56 | 4.07 | 3.37 |
| radiation | Mo K$_2$ | Mo K | Mo K |
| R | 0.067 | 0.047 | 0.054 |
| R$_w$ | 0.110 | 0.049 | 0.061 |

Piperazinylmethylenesulfonic acid, FIG. 3B. A colorless parallelepiped crystal was mounted in a thin-walled glass capillary under an inert atmosphere of argon. Cell parameters and an orientation matrix for data collection, obtained from a least-squares refinement of the setting angles of 25 carefully centered reflections corresponded to a monoclinic cell. The space group was determined to be C2/c. The structure was solved by direct methods and refined on the basis of 1221 observed reflections with I>3σ(I) using SDP.

Non-hydrogen atoms were refined using anisotropic thermal parameters. Hydrogen atoms were calculated at idealized positions included in the calculations but not refined. Least-squares refinement converged at $R=0.067$ and $R_w=0.110$. Final atomic coordinates are given in Table III. Selected distances and angles are given in Table IV.

TABLE III

Atomic Coordinates and Their Equivalent Isotropic Thermal Parameters FIG. 3B

| Atom | X | Y | Z | B(A2) |
|---|---|---|---|---|
| S | 0.6210(1) | 0.1276(3) | 0.1062(1) | 1.48(3) |
| O1 | 0.6895(3) | 0.2570(8) | 0.1588(4) | 1.9(1) |
| O2 | 0.6505(4) | −0.0370(8) | 0.0613(4) | 2.8(1) |
| O3 | 0.5719(3) | 0.0739(9) | −0.1694(4) | 2.9(1) |
| N1 | 0.5833(3) | 0.3689(9) | −0.0657(4) | 1.4(1) |
| N2 | 0.6746(4) | 0.525(1) | −0.1837(4) | 2.0(1) |
| C1 | 0.5528(4) | 0.271(1) | 0.0064(5) | 1.6(1) |
| C2 | 0.6084(5) | 0.240(1) | −0.1347(5) | 2.1(2) |
| C3 | 0.6172(5) | 0.360(1) | −0.2228(5) | 2.3(2) |
| C4 | 0.6493(5) | 0.651(1) | −0.1110(6) | 2.4(2) |
| C5 | 0.6427(4) | 0.525(1) | −0.0244(5) | 1.9(1) |

Anisotropically refined atoms are given in the form of the isotropic equivalent displacement parameter defined as: $(4/3) * [a^2 * B(1,1) + b^2 * B(2,2) + c^2 * B(3,3) + ab(\cos \gamma) * B(1,2) + ac(\cos \beta) * B(1,3) + bc(\cos \alpha) * B(2,3)]$

TABLE IV

Selected Bond Distance (Å) and Angles (deg.) for FIG. 3B

Distances

| | | | | | |
|---|---|---|---|---|---|
| S-O(1) | 1.484(5) | N(1)-C(1) | 1.44(1) | N(2)-C(4) | 1.49(1) |
| S-O(2) | 1.454(6) | N(1)-C(2) | 1.47(1) | C(2)-C(3) | 1.52(1) |
| S-O(3) | 1.458(7) | N(1)-C(5) | 1.473(9) | C(4)-C(5) | 1.51(1) |
| S-(C1) | 1.809(7) | N(2)-C(3) | 1.50(1) | | |

Angles

| | | | |
|---|---|---|---|
| O(1)-S-O(2) | 109.2(3) | C(2)-N(1)-C(5) | 111.5(6) |
| O(1)-S-O(3) | 113.0(3) | C(3)-N(2)-C(4) | 111.7(6) |
| O(1)-S-C(1) | 107.2(3) | S-C(1)-N(1) | 119.0(5) |
| O(2)-S-O(3) | 114.9(4) | N(1)-C(2)-C(3) | 109.6(6) |
| O(2)-S-C(1) | 109.0(3) | N(2)-C(3)-C(2) | 109.7(5) |
| O(3)-S-C(1) | 103.0(3) | N(2)-C(4)-C(5) | 109.1(6) |
| C(1)-N(1)-C(2) | 115.6(6) | N(1)-C(5)-C(4) | 108.7(5) |
| C(1)-N(1)-C(5) | 115.7(5) | | |

Hydrogen sodium 1,4,7-triazacyclononane-N,N'-bis(-methylenesulfonate), FIG. 5A. A crystalline sample was prepared for X-ray examination in the same manner as employed for FIG. 3B. Cell parameters obtained as before corresponded to an orthorhombic cell. The space group was determined to be Pna2$_1$. Structure solution and refinement based upon 1271 reflections with $I>3\sigma(I)$ converged with $R=0.047$ and $R_w=0.049$. Final atomic coordinates are given in Table V. Selected distances and angles are given in Table VI.

TABLE V

Atomic Coordinates and Their Equivalent Isotropic Thermal Parameters for FIG. 5A

| | | | | |
|---|---|---|---|---|
| S1 | 0.1566(1) | 0.4184(2) | 0.290 | 1.63(3) |
| S2 | −0.0177(1) | −0.2573(2) | 0.3768(3) | 1.94(3) |
| NA | −0.0055(2) | 0.5413(3) | 0.0304(5) | 2.55(6) |
| O1 | 0.2333(3) | 0.4530(6) | 0.2582(8) | 2.7(1) |
| O2 | 0.1051(3) | 0.4927(6) | 0.1920(9) | 3.0(1) |
| O3 | 0.1383(3) | 0.4275(6) | 0.4644(7) | 2.3(1) |
| O4 | −0.0430(3) | −0.3597(7) | 0.276(1) | 3.8(1) |
| O5 | 0.0238(3) | −0.3110(6) | 0.5201(8) | 2.7(1) |
| O6 | −0.0649(4) | −0.1551(6) | 0.413(1) | 4.2(1) |
| O7 | 0.0427(3) | 0.7088(6) | −0.1382(9) | 3.3(1) |
| O8 | 0.3610(4) | 0.4242(7) | 0.4378(9) | 3.7(1) |
| N1 | 0.1841(3) | 0.1500(6) | 0.3224(8) | 1.6(1) |
| N2 | 0.1164(3) | −0.1096(6) | −0.3451(8) | 1.6(1) |
| N3 | 0.2573(3) | −0.0773(7) | 0.2204(8) | 1.9(1) |
| C1 | 0.1450(4) | 0.2477(7) | 0.232(1) | 1.7(1) |
| C2 | 0.0609(4) | −0.1812(8) | 0.258(1) | 1.8(1) |
| C3 | 0.2657(4) | 0.1531(8) | 0.317(1) | 2.0(1) |
| C4 | 0.2963(4) | 0.0141(7) | 0.334(1) | 2.0(2) |
| C5 | 0.2377(4) | −0.2082(7) | 0.287(1) | 2.4(1) |
| C6 | 0.1763(4) | 0.1903(7) | 0.413(1) | 1.7(1) |
| C7 | 0.0891(4) | 0.0013(7) | 0.443(1) | 1.9(1) |
| C8 | 0.1494(4) | 0.1071(7) | 0.473(1) | 2.0(1) |

Anisotropically refined atoms are given in the form of the isotropic equivalent displacement parameter defined as: $(4/3) * [a^2 * B(1,1) + b^2 * B(2,2) + c^2 * B(3,3) + ab(\cos \gamma) * B(1,2) + ac(\cos \beta) * B(1,3) + bc(\cos \alpha) * B(2,3)]$

TABLE VI

Selected Bond Distance (Å) and Angles (deg.) for FIG. 5A

Distances

| | | | | | |
|---|---|---|---|---|---|
| S(1)-O(1) | 1.446(6) | S(2)-C(2) | 1.808(8) | N(3)-C(4) | 1.49(1) |
| S(1)-O(2) | 1.441(7) | N(1)-C(1) | 1.43(1) | N(3)-C(5) | 1.48(1) |
| S(1)-O(3) | 1.484(6) | N(1)-C(3) | 1.467(9) | C(3)-C(4) | 1.52(1) |
| S(1)-C(1) | 1.810(8) | N(1)-C(8) | 1.46(1) | C(5)-C(6) | 1.53(1) |
| S(2)-O(4) | 1.444(7) | N(2)-C(2) | 1.43(1) | C(7)-C(8) | 1.55(1) |
| S(2)-O(5) | 1.453(7) | N(2)-C(6) | 1.464(9) | | |
| S(2)-O(6) | 1.442(7) | N(2)-C(7) | 1.47(1) | | |

Angles

| | | | |
|---|---|---|---|
| O(1)-S(1)-O(2) | 112.5(4) | C(3)-N(1)-C(8) | 117.3(6) |
| O(1)-S(1)-O(3) | 111.8(3) | C(2)-N(2)-C(6) | 115.0(6) |
| O(1)-S(1)-C(1) | 107.1(3) | C(2)-N(2)-C(7) | 115.7(6) |
| O(2)-S(1)-O(3) | 111.8(4) | C(6)-N(2)-C(7) | 117.5(6) |
| O(2)-S(1)-C(1) | 106.2(4) | C(4)-N(3)-C(5) | 115.8(6) |
| O(3)-S(1)-C(1) | 107.0(3) | S(1)-C(1)-N(1) | 118.0(5) |
| O(4)-S(2)-O(5) | 111.7(4) | S(2)-C(2)-N(2) | 116.4(6) |
| O(4)-S(2)-O(6) | 112.3(4) | N(1)-C(3)-C(4) | 109.8(6) |
| O(4)-S(2)-C(2) | 106.0(4) | N(3)-C(4)-C(3) | 110.5(6) |
| O(5)-S(2)-O(6) | 113.0(4) | N(3)-C(5)-C(6) | 108.6(6) |
| O(5)-S(2)-C(2) | 106.7(3) | N(2)-C(6)-C(5) | 109.5(6) |
| O(6)-S(2)-C(2) | 106.5(4) | N(1)-C(7)-C(8) | 112.7(6) |
| C(1)-N(1)-C(3) | 117.4(6) | N(1)-C(8)-C(7) | 111.8(7) |
| C(1)-N(1)-C(8) | 116.5(6) | | |

1,4,7,10-tetraazacyclododecane-N,N''-bis(methylenesulfonic acid), FIG. 6. A single crystal was prepared for X-ray examination as described above. Cell parameters and an orientation matrix corresponded to a monoclinic cell. The space group was determined to be P2$_1$/n. Structure solution and refinement based upon 1300 reflections with $I>3\sigma(I)$ converged with $R=0.054$ and $R_w=0.061$. Final atomic coordinates are given in Table VII. Selected distances and angles are given in table VIII.

TABLE VII

Atomic Coordinates and Their Equivalent Isotropic Thermal Parameters

| Atom | X | Y | Z | 8 (A2) |
|---|---|---|---|---|
| S1 | 0.2121(2) | 0.4527(2) | 0.8832(2) | 2.00(4) |
| S2 | −0.3597(2) | 0.4762(2) | 0.6338(2) | 1.94(4) |
| O1 | 0.3226(6) | 0.4726(5) | 0.8152(4) | 3.2(1) |
| O2 | 0.2348(6) | 0.5109(5) | 0.9702(4) | 2.8(1) |
| O3 | 0.1942(6) | 0.3480(4) | 0.9041(4) | 2.7(1) |
| O4 | −0.2868(6) | 0.4585(4) | 0.7280(4) | 3.0(1) |
| O5 | −0.4563(6) | 0.3975(4) | 0.5992(4) | 3.0(1) |
| O6 | −0.2561(7) | 0.5040(5) | 0.5645(5) | 3.5(1) |
| O7 | 0.0237(7) | 0.6294(5) | 0.4709(4) | 3.4(1) |
| O8 | 0.2640(8) | 0.8861(7) | 0.8622(6) | 6.2(2) |
| N1 | 0.0149(7) | 0.5925(5) | 0.8049(5) | 1.8(1) |
| N2 | −0.2793(7) | 0.6166(4) | 0.8686(4) | 1.5(1) |
| N3 | −0.3870(7) | 0.665(5) | 0.6792(5) | 1.9(1) |
| N4 | −0.0924(7) | 0.6943(5) | 0.6362(5) | 2.1(1) |
| C1 | 0.0369(9) | 0.4890(6) | 0.8238(6) | 2.1(2) |
| C2 | −0.4770(9) | 0.5796(5) | 0.6464(6) | 1.9(2) |
| C3 | −0.0126(9) | 0.6519(6) | 0.8900(6) | 2.2(2) |
| C4 | −0.1670(9) | 0.6957(6) | 0.8818(5) | 1.8(2) |
| C5 | −0.4308(9) | 0.6557(7) | 0.8492(6) | 2.3(2) |
| C6 | −0.4470(9) | 0.7170(6) | 0.7588(5) | 1.9(2) |
| C7 | −0.354(1) | 0.7279(6) | 0.5974(6) | 2.5(2) |
| C8 | −0.203(1) | 0.7750(6) | 0.6153(7) | 2.5(2) |

TABLE VII-continued

Atomic Coordinates and Their Equivalent Isotropic Thermal Parameters

| Atom | X | Y | Z | 8 (A2) |
|---|---|---|---|---|
| C9  | 0.0439(9) | 0.7268(6) | 0.6921(6) | 2.3(2) |
| C10 | 0.1132(9) | 0.6383(6) | 0.7415(6) | 2.1(2) |

TABLE VIII

Elected Bond Distances (Å) and Angles (deg.)

Distances

| | | | | | |
|---|---|---|---|---|---|
| S(1)-O(1) | 1.464(6) | N(1)-C(1)  | 1.44(1) | N(4)-C(8) | 1.51(1) |
| S(1)-O(2) | 1.455(6) | N(1)-C(3)  | 1.48(1) | N(4)-C(9) | 1.49(1) |
| S(1)-O(3) | 1.464(6) | N(1)-C(10) | 1.45(1) | C(3)-C(4) | 1.53(1) |
| S(1)-C(1) | 1.821(8) | N(2)-C(4)  | 1.49(1) | C(5)-C(6) | 1.52(1) |
| S(2)-O(4) | 1.456(6) | N(2)-C(5)  | 1.49(1) | C(7)-C(8) | 1.52(1) |
| S(2)-O(5) | 1.449(6) | N(3)-C(2)  | 1.48(1) | C(9)-C(10)| 1.50(1) |
| S(2)-O(6) | 1.455(7) | N(3)-C(6)  | 1.46(1) | | |
| S(2)-C(2) | 1.785(8) | N(3)-C(7)  | 1.48(1) | | |

Angles

| | | | |
|---|---|---|---|
| O(1)-S(1)-O(2) | 112.5(4) | C(4)-N(2)-C(5) | 112.9(6) |
| O(1)-S(1)-O(3) | 113.7(4) | C(2)-N(3)-C(6) | 112.6(6) |
| O(1)-S(1)-C(1) | 106.2(4) | C(2)-N(3)-C(7) | 110.7(6) |
| O(2)-S(1)-O(3) | 111.8(4) | C(6)-N(3)-C(7) | 115.1(6) |
| O(2)-S(1)-C(1) | 107.7(4) | C(8)-N(4)-C(9) | 114.4(6) |
| O(3)-S(1)-C(1) | 104.2(4) | S(1)-C(1)-N(1) | 117.0(5) |
| O(4)-S(2)-O(5) | 114.2(4) | S(2)-C(2)-N(3) | 108.9(5) |
| O(4)-S(2)-O(6) | 111.7(4) | N(1)-C(3)-C(4) | 111.3(6) |
| O(4)-S(2)-C(2) | 106.2(4) | N(2)-C(4)-C(3) | 110.7(6) |
| O(5)-S(2)-O(6) | 112.3(4) | N(2)-C(5)-C(6) | 112.5(6) |
| O(5)-S(2)-C(2) | 104.9(3) | N(3)-C(6)-C(5) | 110.8(6) |
| O(6)-S(2)-C(2) | 106.7(4) | N(3)-C(7)-C(8) | 110.4(7) |
| C(1)-N(1)-C(3) | 114.5(6) | N(4)-C(8)-C(7) | 108.3(6) |
| C(1)-N(1)-C(10)| 116.6(6) | N(4)-C(9)-C(10)| 108.3(6) |
| C(3)-N(1)-C(10)| 114.2(6) | N(1)-C(10)-C(9)| 111.4(7) |

EXAMPLE 3

Mechanisms of Sulfomethylation and Hydrolysis

The Mannich reaction—The sulfomethylation of amines by a Mannich-type reaction with formaldehyde and sodium bisulfite has been known for many years (Gilbert; Knoevenagel, (1904,37); Reinking et al., Bucherer et al., Backer et al. 1934; Neelakantan et al.). Recently, the crystal structure of dimethylaminomethylene sulfonic acid (FIG. 2A) was reported and its shows that a C—S bond is indeed formed (Burg). Aminomethylenesulfonates (Lauffer) are unstable in aqueous solution, as an equilibrium is formed (see FIG. 9) (Burg; Stewart et al.). The reverse Mannich reaction, i.e., the formation of the sulfite ion is slow with respect to the reaction of sulfite with the iminium ion (Stewart et al.).

The reaction rate of the reverse Mannich is enhanced by increasing the temperature. (Monomethylaminomethylenesulfonic acid, for example, at 30° C. gives a 80% purity upon base titration, while at 5° C. the measured purity was 98%; Falk et al.) At 25° C., the amount of free sulfite ion at equilibrium is usually less than one percent for disubstituted amines (Stewart et al.).

Figure 10:
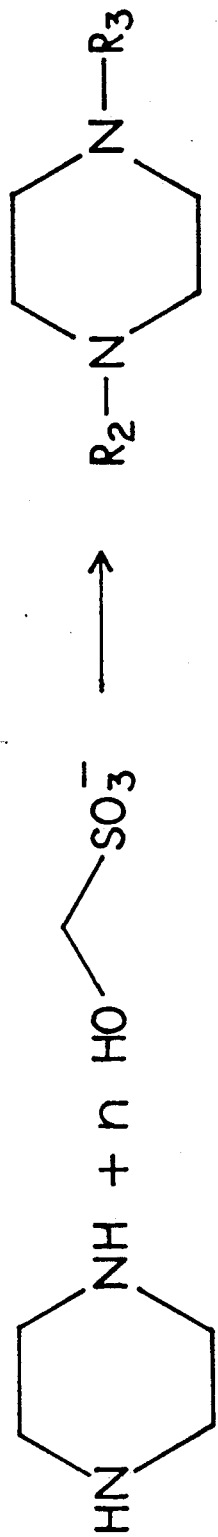
FIG. 10. Disulfomethylation of piperazine at pH 10.
Figure 11:
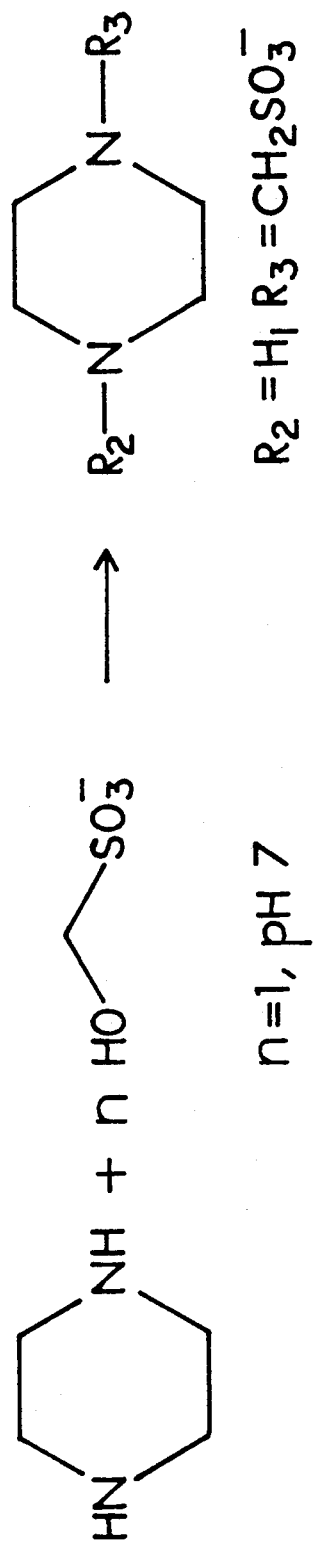
FIG. 11. Sulfomethylation of piperazine at pH 7.

Sulfomethylation of piperazine—As shown in FIG. 10, piperazine may be disulfomethylated using 2 moles of commercially available formaldyhyde sodium bisulfite at 40° C. for 15 minutes in a concentrated aqueous solution. Disodium piperazine-N,N'-bis(methylenesulfonate) (FIG. 3A) crystallizes upon formation in 51% yield. Piperazinylmethylenesulfonic acid (FIG. 3B) can be prepared selectively in 51% yield by decreasing the pH of the reaction mixture to 7.0 (FIG. 11). Under these conditions, even a 3-fold excess of formaldyhyde sodium bisulfite results in formation of the monosubstituted product exclusively.

Figure 12:
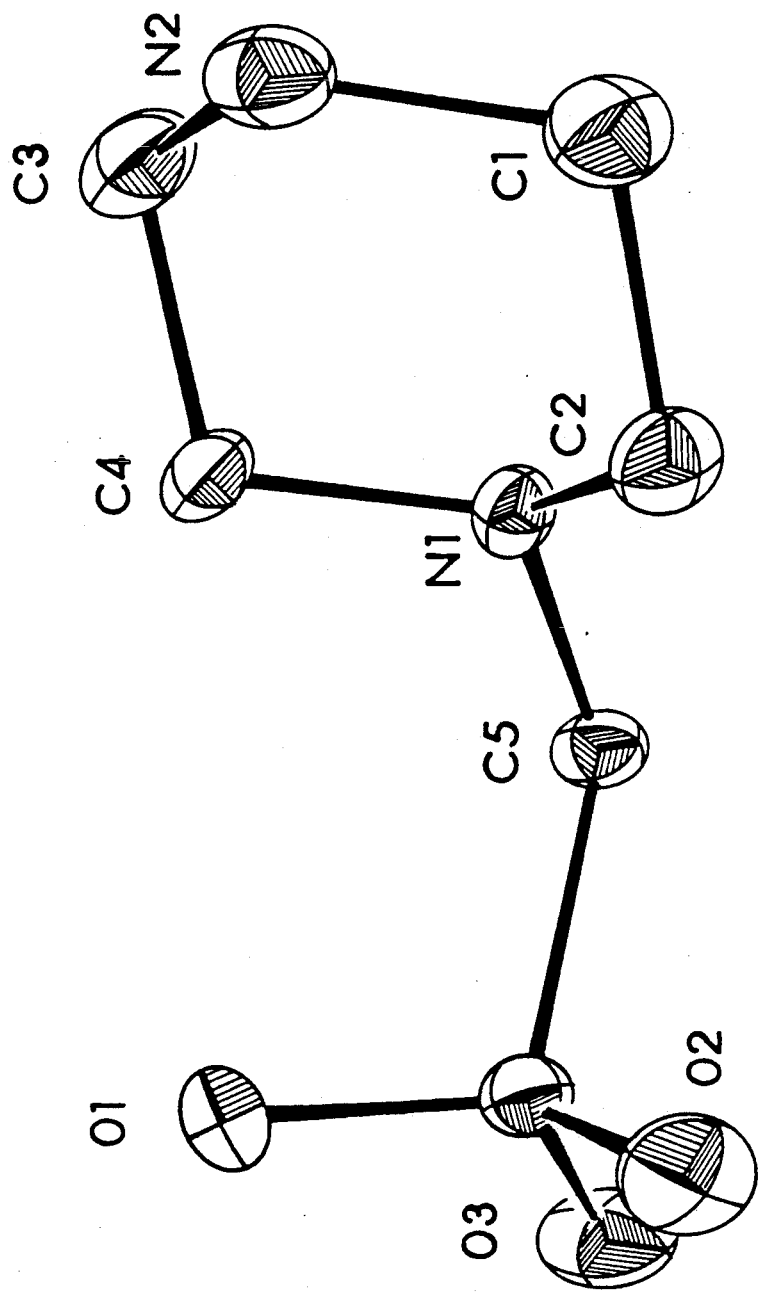
FIG. 12. The structure of piperazinylmethylenesulfonic acid, as determined by x-ray crystallography.

The structure of FIG. 3B has been confirmed by X-ray crystallography, FIG. 12. This structure shows that the formation of a sulfamide between the free amine and the sulfonate group as reported for aromatic amines (Neelakanta et al. does not occur.

Figure 13:
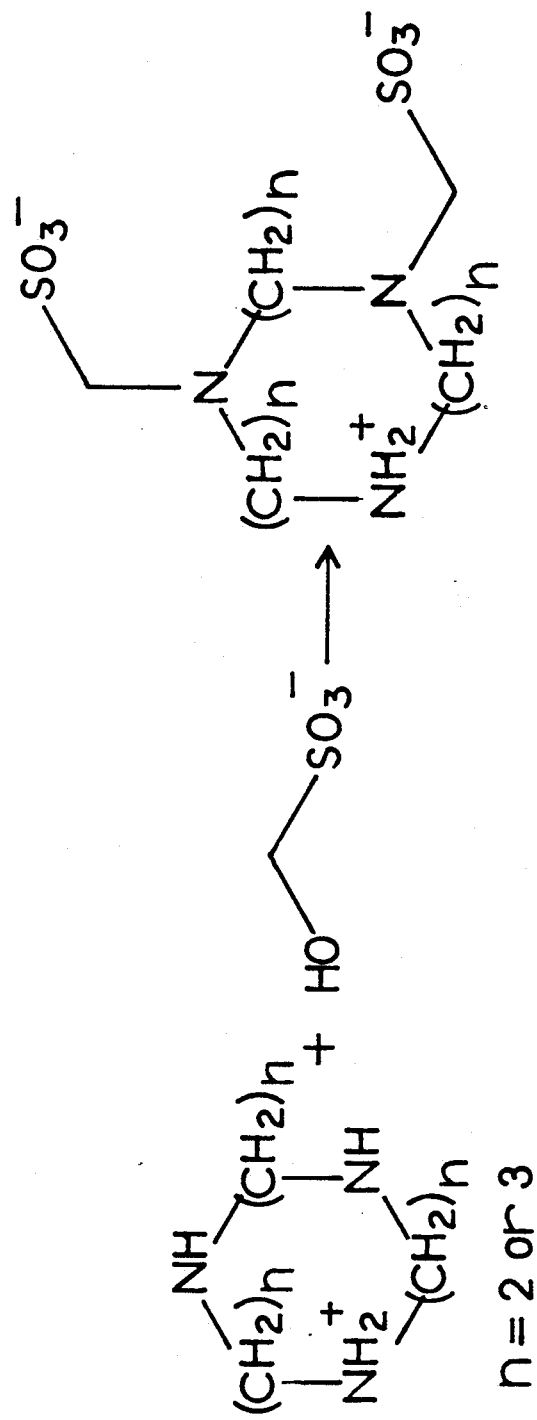
FIG. 13. Sulfomethylation of polyazamacrocycles [9]aneN3 and [12]andN3 yields only the disulfomethylated product at pH 7 (and only the monosulfomethylated product at pH 4).
Figure 14:
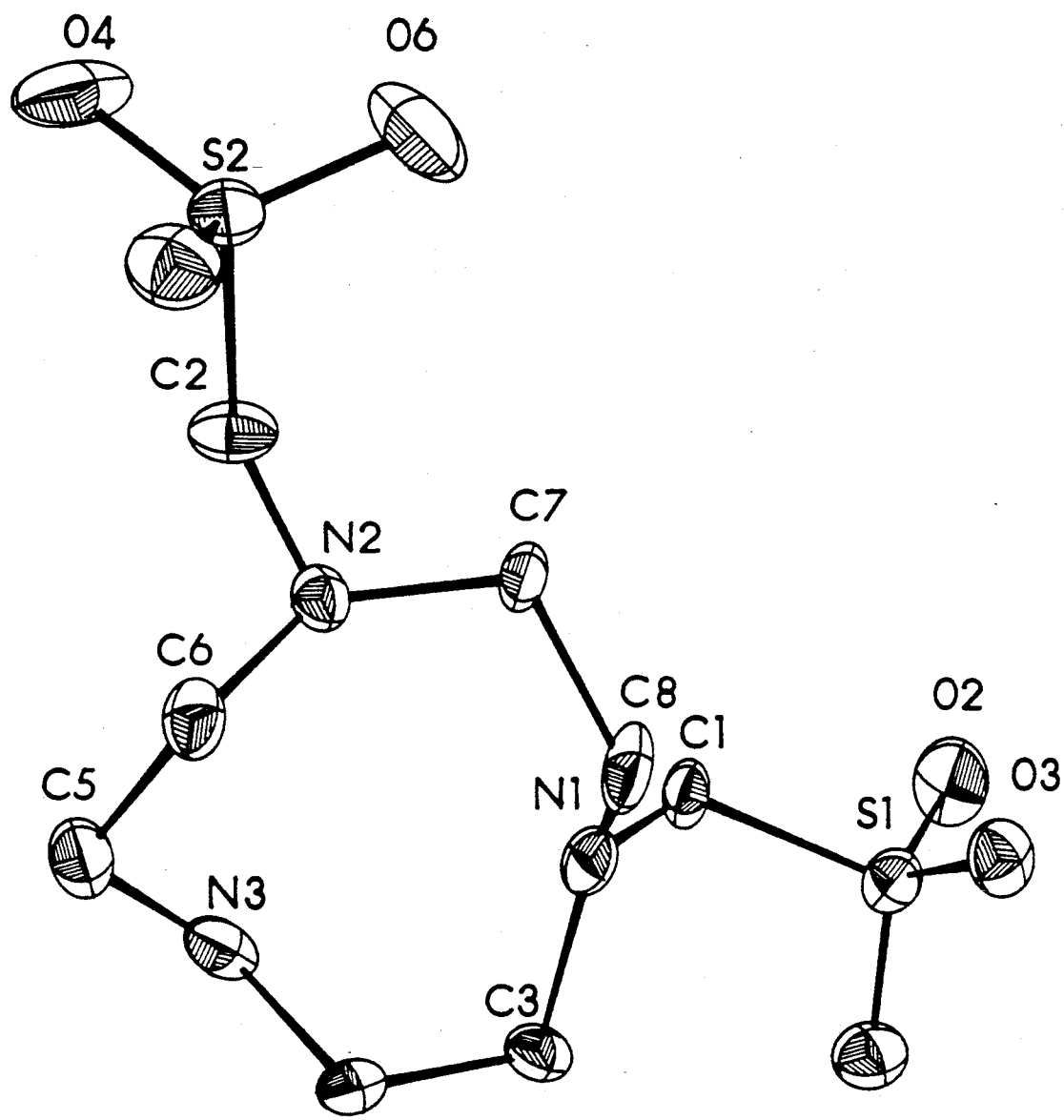
FIG. 14. The structure of hydrogen sodium 1,4,7-triazacyclononane-N,N'-bis(methylenesulfonate), as determined by x-ray crystallography.

Sulfomethylation of polyazamacrocycles—A similar pH selectivity is observed for sulfomethylation of polyazamacrocycles, FIG. 13. With formaldyhyde sodium bisulfite in excess (3 moles per nitrogen), only the monosulfomethylated product is formed at pH 4 (16 hours at 40° C.) while the disulfomethylated product is formed exclusively at pH 7. Disulfomethylated [9]aneN3 (FIG. 13, n=2) and [12]aneN3 (FIG. 13, n=3) may be obtained in high yields by using exactly stoichiometric amounts of formaldyhyde sodium bisulfite at neutral pH (16 hours at 40° C.). For disulfomethylated [9]aneN3, the structure of the anion (FIG. 14) was confirmed by X-ray crystallography.

When the pH is increased to 11.8, trisubstituted [12]aneN3 is the main product formed. Prolonged heating of the pH 11.8 reaction mixture leads to extensive decomposition of the trisulfomethylated compound.

The results described thusfar indicate that protonation of a secondary amine inhibits its reactivity towards sulfomethylation. The distinct $pK_a$ differences of the nitrogens in the polyazamacrocycles then give rise to the unusual selectivity described above. The predominant protonated species of [12]aneN3 present at pH 4, for example, is [12]aneN3.2H$^+$, while at pH 7 the dominant species is [12]aneN3.H$^+$ (Table I).

Figure 16:
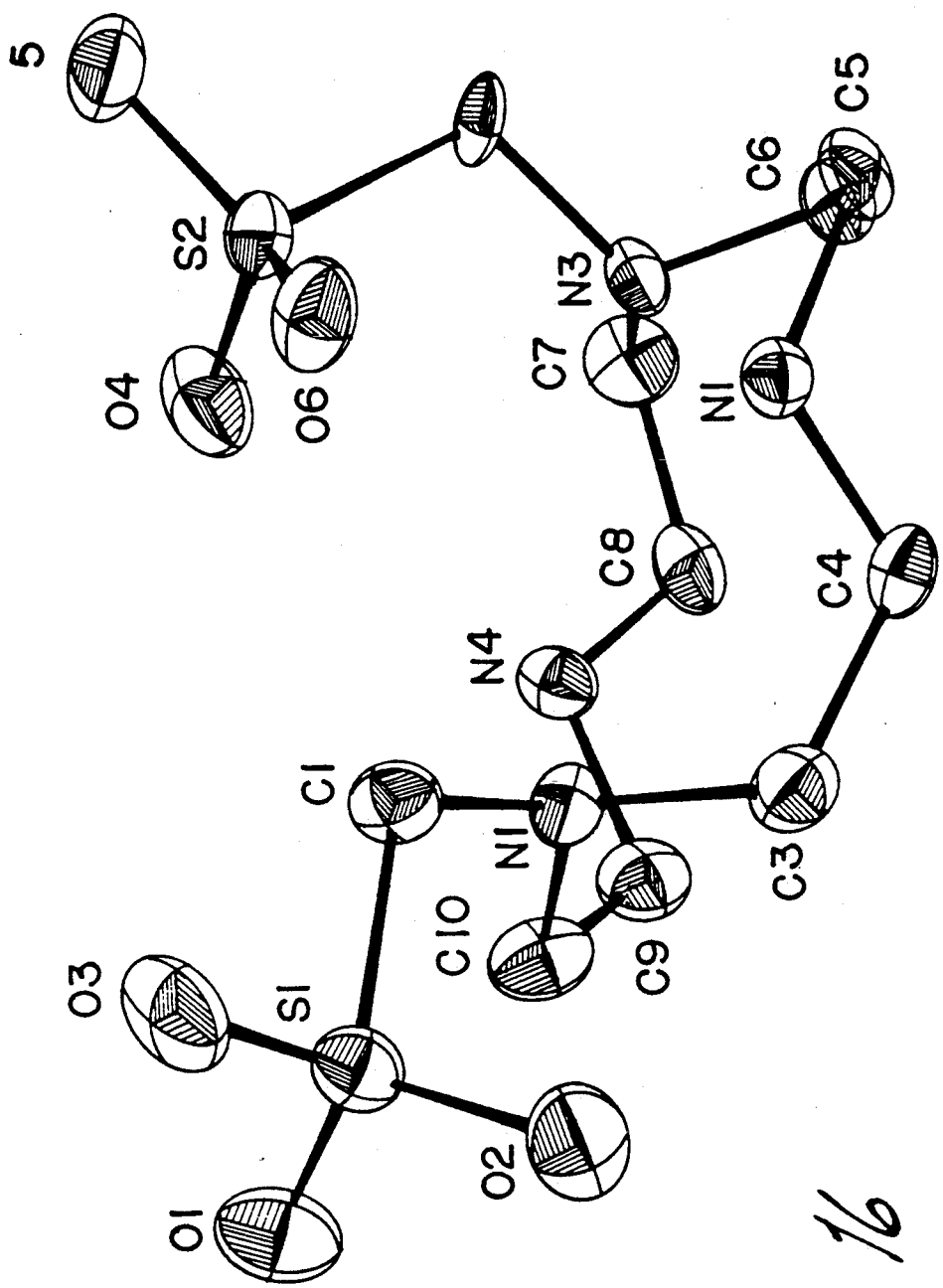
FIG. 16. Structure of 1,4,7,10-tetraazacyclododecane-N,N''-bis(methylenesulfonic acid) confirmed by X-ray crystallography.

Sulfomethylation of the tetraazamacrocycle [12]aneN4—This macrocycle has two high and two low pKa values (Table I) so at neutral pH, [12]aneN4.2H$^+$ is virtually the only ionic form present. Sulfomethylation of this amine at pH 7 thus yields the disulfomethylated product exclusively (FIG. 15). Of the two possible regioisomers, the 1,7 isomer shown in FIG. 15 is the predominant product (>90%), as judged by $^{13}$C NMR. This regioselectivity of the sulfomethylation reaction confirms the micro protonation sequence for [12]aneN4, as determined by NMR. Recrystallization of the product in ethanol/water gives 1,4,7,10-tetraazacyclododecane-N,N''-bis(methylenesulfonic acid) in pure form, while X-ray study of a single crystal confirms its structure (FIG. 16).

Sulfomethylation of the hexaazamacrocycle [18]aneN6—Regioisomers can also be formed in [18]aneN6. The reaction of [18]aneN6 with 3 moles of formaldehyde sodium bisulfite at pH 7 gives the 1,7,13-trisubstituted derivative 1,4,7,10,13,16-hexaazacyclooctadecane-N,N'',N''''-tris(methylenesulfonate) as the main product (FIG. 17). When this reaction is carried out in a Na$_2$PO$_4$ and KH$_2$PO$_4$ buffer, the same product crystallizes from the reaction mixture as a HPO$_4{}^{2-}$ adduct.

Monosubstituted products from sulfomethylation of the macrocycles [9]aneN3 and [12]aneN3—As indicated above, the monosubstituted product 1,5,9-triazacyclododecane-N-methylenesulfonate hydrotriiodide may be synthesized at pH 4 in the presence of a large excess of formaldehyde sodium bisulfite. If only 1.5 moles of the latter per mole of [12]aneN3 are used, only about 30% of the [12]aneN3 is converted to the monosubstituted product over a period of 16 hours at 50° C. The rates of similar sulfomethylation reactions are known to drop substantially at lower pH values (Gilbert). Longer reaction times at 50° C. lead to extensive decomposition of the desired product, as indicated by $^{13}$C NMR.

Alternatively, dimethylaminomethylenesulfonic acid (FIG. 2A) may be used as a sulfomethylating agent via an amine exchange reaction (FIG. 18). Equimolar amounts of dimethylaminomethylenesulfonic acid and [9]aneN3 or [12]aneN3 at pH 3.5 give complete conversion to 1,4,7-triazacyclononane-N-methylenesulfonate hydrotriiodide or 1,5,9-triazacyclododecane-N-methylenesulfonate hydrotriiodide, plus the dimethylammonium ion after 16 hours at 25° C., as indicated by NMR. The large pK differences between dimethylamine and the pK$_3$'s of [9]aneN3 or [12]aneN3 (Table I) results in an equilibrium which lies toward the monosulfomethylated macrocycle at this pH. This is nicely illustrated by the sulfomethylation of piperazine with an excess of dimethylaminomethylenesulfonic acid at pH 11 for several days at 25° C.; a 1:1 mixture of disodium piperazine-N,N'-bis(methylenesulfonate) and piperazinylmethylenesulfonic acid is formed. This indicates that the pK$_a$ difference between dimethylamine and pK$_1$ of piperazine is too small to lead to a high selectivity for the amine-exchange reaction (Table I).

Figure 9:
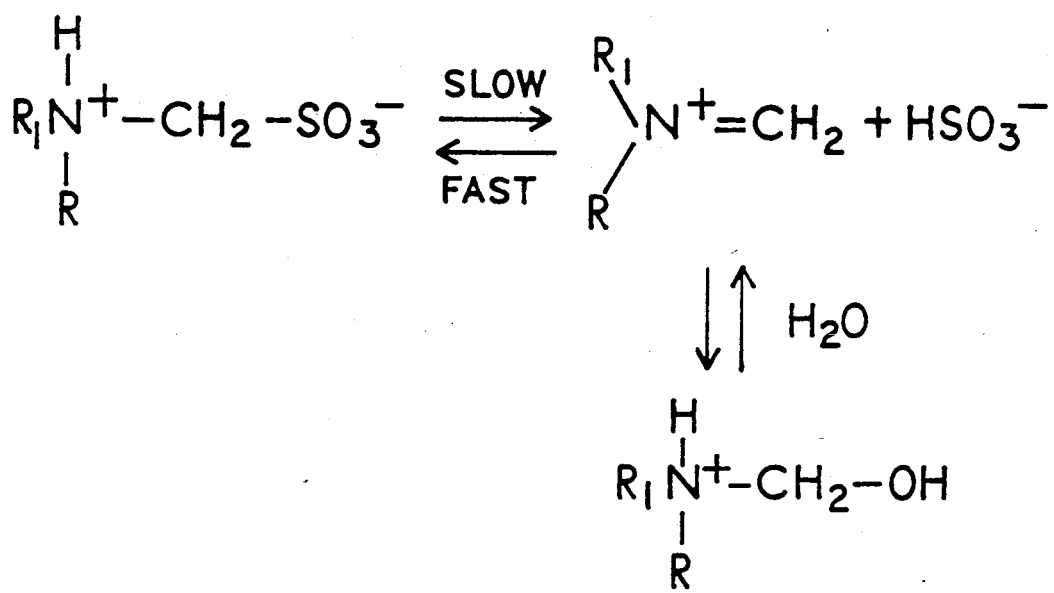
FIG. 9. Reverse as well as forward Mannich-type reactions occur because aminomethylenesulfonates are unstable in aqueous solution.

Another example of results expected with small pK$_a$ differences is seen in the work of Neelakantan and Hartung (Neelakantan et al.), showing that amine exchange between the phenylmethylenesulfonate of aniline and p-methylaniline gives a mixture of products. The commercially available aminomethylenesulfonic acid (FIG. 2B) undergoes a similar amine exchange reaction but the rate of exchange is slower. After stirring at 25° C. for 16 hours, 50% of [9]aneN3 is converted to 1,4,7-triazacyclononane-N-methylenesulfonate hydrotriiodide using a slight excess of aminomethylenesulfonc acid (1.3 moles) per mole of [9]aneN3. The rate of exchange might be effected by the low solubility of aminomethylenesulfonic acid, since it slowly dissolves during the course of the reaction. (The aminomethylenesulfonic acid does not dissolve totally using a 3.5 moles excess.) The amine-exchange reaction likely occurs via the reverse Mannich reaction (FIG. 9). The iminium ion or its hydrated form can react with a nonprotonated triazamacrocyclic amine to liberate the dimethylammonium ion. The resulting macrocyclic iminium ion can then react with a sulfite ion to form the observed monosubstituted product. Monoalkylation of tri- and tetraazamacrocycles normally requires a 5-fold excess of cyclic amine over the alkylating agent (Alcock et al.; Kruper et al.; Cox et al.), whereas formaldehyde sodium bisulfite and dimethylaminomethylenesulfonic acid may be used in equimolar amounts.

Figure 19:
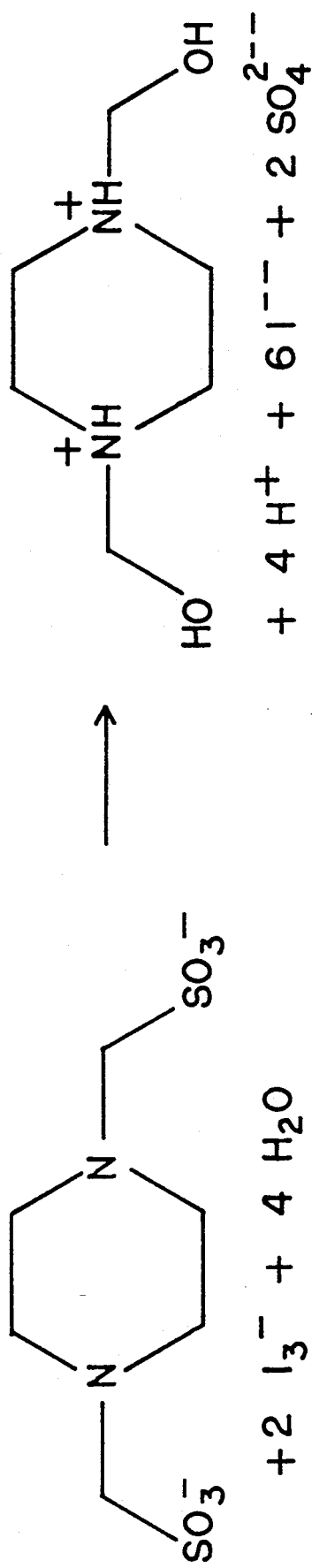
FIG. 19. Oxidative hydrolysis of disubstituted aminomethylenesulfonic acids to aminomethanol derivatives by triiodide.

Oxidative hydrolysis of aminomethylenesulfonates by triiodide—Stewart and Bradley (Stewart et al.) have shown that disubstituted aminomethylenesulfonic acids can undergo oxidative hydrolysis to aminomethanol derivatives by reaction with triiodide (FIG. 19). The reaction rate is first order in aminomethylenesulfonic acid and independent of the triiodide concentration (Stewart et al.). The rate limiting step in this reaction is the formation of the sulfite ion via the reverse Mannich reaction (FIG. 9) prior to its oxidation to sulfate. $^1$H NMR studies by Burg (Burg) have shown that the reaction of triiodide with dimethylaminomethylenesulfonic acid proceeds almost quantitatively to dimethylaminomethanol within a few minutes, as judged by the HOCH$_2$NMe$_2$ resonances observed at 4.56 ppm and 2.78 ppm. Similarly, the reaction of disodium piperazine-N,N'-bis(methylenesulfonate) with 2 moles of triiodide in aqueous solution at 25° C. results in a change in color from brown to colorless after 2 minutes.

This event is followed by the formation of a white precipitate, which is isolated in 44% yield. An IR spectrum of the isolated solid shows a broad absorption from 2534–2342 cm$^{-1}$, indicative of a protonated quaternary nitrogen. Elemental analysis indicates the formation of the dihydrated from of the diiminium ion (FIG. 19), which upon dissolution in D$_2$O is partially hydrolyzed to the monosubstituted analog as shown by $^1$H NMR.

Addition of sodium triiodide solution to either of the macrocyclic monosulfomethylated products gives brown precipitates in high yields. These are the triiodide salts, which have limited water solubility at room temperature. The triiodide salt of 1,4,7-triazacyclononane-N-methylenesulfonate, however, fully dissolves in water at 40° C. after an extended period of 3 hours and the solution becomes colorless indicating that triiodide has reacted with the monosulfomethylated amine.

Oxidative hydrolysis may be confirmed by $^1$H NMR which shows broad peaks for the [9]aneN3 protons (3.61 ppm) and the N—CH$_2$OH methylene protons (4.58 ppm). Sharp signals at 4.81 and 3.69 ppm indicate some further hydrolysis to HOCH$_2$OH and unsubstituted [9]aneN3. Dissolution and subsequent reaction of 1,4,7-triazacyclododecane-N-methylenesulfonate goes even slower as no fully completed oxidative hydrolysis is obtained at 40° C. in aqueous solution after 16 hours.

It also proved possible to reduce the triiodide anion of 1,4,7-triazacyclononane-N-methylenesulfonate to an iodide anion without altering the methylenesulfonate group on the macrocycle by suspending the salt in ethanol and adding excess diethyl phosphite.

EXAMPLE 4

Conversion of Aminomethylenesulfonates to Aminomethylenecarboxylates

The conversion of aminomethylenesulfonates to amino acids via nucleophilic substitution of cyanide for sulfonate has been known for decades (FIG. 20) (Knoevenagel, E.; Knoevenagel, E. (1904, 89); Miller et al.; Neelakantan et al.). Cyanide substitution can be performed without isolation of the sulfomethylated product by adding NaCN directly to the reaction mixture with continuous stirring for several hours at 25° C. (Neelakantan et al.). Preparation of the monosubstituted product proceeds smoothly with a 1.4-fold excess of dimethylaminomethylenesulfonic acid over [9]aneN3, followed by 1.5-fold excess of NaCN (FIG. 21).

$^{13}$C NMR spectra of the reaction mixture indicates that N-cyanomethyl-1,4,7-triazacyclononane is the main product formed in the reaction of FIG. 21, with about 15–20% of the unsubstituted [9]aneN3. Both dimethylamine and a small amount of (CH$_3$)$_2$NCH$_2$CN formed by CN$^-$ substitution of the sulfonate moiety of dimethylaminomethylenesulfonic acid are present in the reaction mixture as well. The product can be purified by cation exchange chromatography giving an isolated yield of 32%.

Subsequent acidic hydrolysis of N-cyanomethyl-1,4,7-triazacyclononane to form triazacyclononane-monoacetic acid (FIG. 22) may be studied by $^1$H NMR. Surprisingly, a total decarboxylation takes place when the product is refluxed in 40% HBr for 5 days, whereas refluxing for 30 minutes in 20% HCl results in 25% decarboxylation; lowering the reaction temperature to 65° C. for 24 hours gives the monoacetic acid derivative with only 10% of free [9]aneN3.

The same objective is met using a less acidic HCl solution 7% (2M HCl) and heating the reaction mixture at 95° C. for 7 hours. Reducing either the temperature or the acidity reduce the amount of decarboxylation but leads to extended reaction times for the hydrolysis. Since reformation of at least some [9]aneN3 appears inevitable during acidic hydrolysis of N-cyanomethyl-1,4,7-triazacyclononane, a one-pot synthesis of the monoacetic acid derivative has been developed with the final hydrolysis conditions being 10% HCl at 75° C. for 4 days. Under these conditions, the monoacetic acid derivative may be purified of [9]aneN3 using a cation exchange column with an isolated yield of 30%.

Formaldehyde sodium bisulfite is used for disulfomethylation of the triaza and tetraaza macrocycles. Unlike dimethylaminomethylenesulfonic acid, which reacts with $CN^-$ to form the unreactive $(CH_3)_2NCH_2CN$, formaldehyde sodium bisulfite can form $HOCH_2CN$ under the reaction conditions, as confirmed by $^{13}C$ NMR in a separate experiment. $HOCH_2CN$ is a well known intermediate in the Strecker synthesis and reacts with free amines to give aminomethylenenitriles (Strecker; Ulrich et al.; Smith et al.).

The reactivity of $HOCH_2CN$ might explain the following observation. When [12]aneN3 is sulfomethylated by using 4 moles of formaldehyde sodium bisulfite per mole of [12]aneN3 in a concentrated buffer medium at pH 7, $^{13}C$ NMR indicates that the major product is disulfomethylated [12]aneN3. However, upon addition of 4 moles of NaCN to this same reaction mixture, the tricyanomethylated derivative of [12]aneN3 (FIG. 23) crystallizes from the reaction mixture in 52% yield.

The same phenomenon is observed for [12]aneN4 using 5.5 moles of formaldehyde sodium bisulfite per mole of [12]aneN4 at pH 7 and adding 5.5 moles of NaCN in the second step. The tetracyanomethylated derivative of [12]aneN4 (FIG. 24) crystallizes from the reaction mixture in 61% yield. To maintain the degree of substitution on the macrocycle, the cyanide substitution reaction must be carried out after the formaldehyde sodium bisulfite is completely consumed by sulfomethylation. Fortunately, disulfomethylated derivatives of [9]aneN3, [12]aneN3, and [12]aneN4 can be prepared quantitatively using stoichiometric amounts of formaldehyde sodium bisulfite.

Thus, the pure 1,7-diacetic acid derivative of [12]aneN4 (FIG. 25) may be isolated in 52% yield (after purification by cation exchange chromatography) by reacting [12]aneN4 with 2 equivalents of formaldehyde sodium bisulfite at pH 7, adding NaCN without a reaction work-up, followed by hydrolysis in refluxing 20% HCl for 48 hours. The 1,4-disubstituted regioisomer formed in low amounts during sulfomethylation is not detected by $^1H$ or $^{13}C$ NMR after column purification. Acidic hydrolysis of the dicyanomethylated [12]aneN4 does not appear to require the same mild acidic conditions to prevent decarboxylation, for reasons that are not fully understood. This same sequence is used to prepare the diacetic acid derivative of [12]aneN3 (FIG. 26) in 19% yield with 95% purity. In this case, a small amount of the monoacetic acid derivative is present after purification by cation exchange chromatography.

EXAMPLE 5

Figure 27:
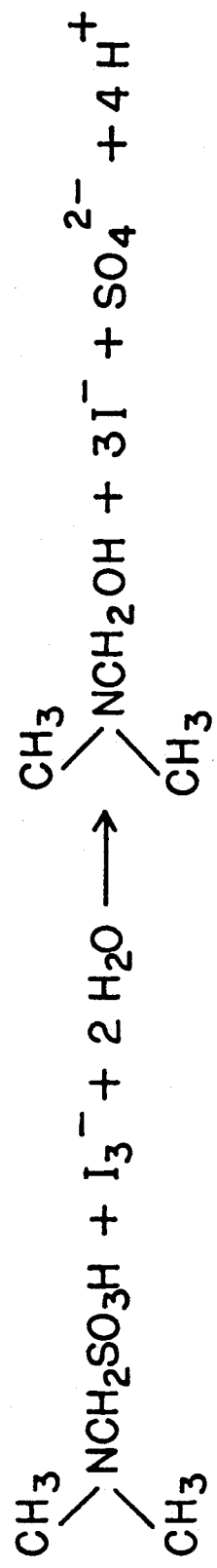
FIG. 27. Oxidative hydrolysis of dimethylaminomethylenesulfonic acid with triiodide in an aqueous solution, during which $(CH_3)_2NCH_2OH$ is formed quantitatively.
Figure 28:
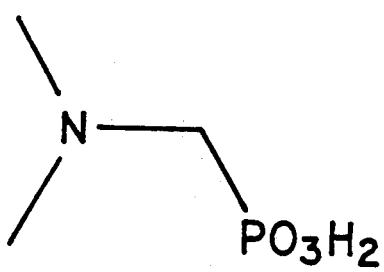
FIG. 28. Dimethylaminomethylenephosphonate.

Conversion of Aminomethylenesulfonates to Aminomethylenephoshonates and Aminomethylenephosphinates Although the mechanism of the cyanide nucleophilic displacement reaction with aminomethylenesulfonates has not been detailed, other strong nucleophiles such as the malonate anion apparently react similarly (Neelakantan et al.). The nucleophilicity of $HP(=O)(OH)_2$ or its conjugated base is too low to displace the sulfonate group as no phosphonylation seems to occur even with a large excess of $HP(=O)(OH)_2$. One sure way to remove the sulfonate is by oxidative hydrolysis with triiodide (Stewart et al.; Burg). Using this method, aminomethylenesulfonates may be converted to the corresponding aminomethanol derivatives, which are reactive intermediates in the Mannich reaction. Upon oxidative hydrolysis of dimethylaminomethylenesulfonic acid with triiodide, $(CH_3)_2NCH_2OH$ is formed quantitatively (as judged by $^1H$ NMR) in an aqueous solution (FIG. 27). Subsequent addition of a 10-fold excess of phosphorous acid yields the desired dimethylaminomethylenephosphonate (FIG. 28) quantitatively after a 4 hours reflux.

Figure 29:
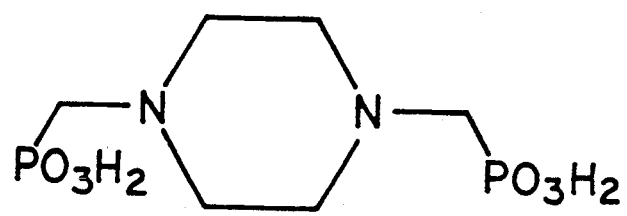
FIG. 29. N,N'-bis(methylenephosphonate) piperazine.

Partial hydrolysis to dimethylammonium and formaldehyde occurs if only a 5-fold excess of phosphorous acid is used. The oxidative hydrolysis of the disulfomethylated derivative of piperazine with triiodide gives a di(hydroxymethyl)piperazine salt that precipitates from solution. Addition of 1 mmol of this salt to a 10M phosphorous acid solution results in the formation of di- (17%) and mono-methylenephosphonate (50%) derivatives of piperazine and piperazine itself after 4 hours at reflux. Removal of the hydroxymethylene groups can be prevented by carrying out the reaction in melted phosphorous acid at 80° C. giving N,N'-bis(methylenephosphonate) piperazine (FIG. 29) as the only product.

The partially substituted methylenesulfonate derivatives of the tri- and tetraaza macrocycles have one additional problem in that the free secondary amino groups can also react with the hydroxymethylene groups to yield polymeric products. To suppress this side reaction, the phosphonylation is carried out in 20% HCl to insure that all amino groups are fully protonated.

The oxidized product of the 1,7-disulfomethylated [12]aneN4 is refluxed with 10-fold excess of phosphorous acid per hydroxymethylene group. Under these reaction conditions, extensive hydrolysis of the hydroxymethylene group still occurs as a mixture of monomethylphosphonylated [12]aneN4 (FIG. 30) is formed with no trace of the expected disubstituted methylenephosphonate. The phosphynylation of the tri- and tetraazamacrocycles cannot be carried out under anhydrous conditions as for the piperazine derivative because their aminomethanol derivatives are not isolated in pure form as a solid.

It appears however that the $HI_3$ salts of the monomethylenesulfonic acids of [9]aneN3 and [12]aneN3 can be used directly. When these triiodide salts are added to melted phosphorous acid at 80° C., at 25° C., $HP(=O)Et(OEt)$, or $HP(=O)(OEt)_2$, a very exothermic reaction occurs whereby the respective monomethylenephosphonate, the monomethylene(ethyl)- phosphinate ethyl ester and the monomethylenephosphonate diethyl ester of [9]aneN3 (FIGS. 31A, 31B, and 31C) and the monomethylenephosphonate diethyl ester and the monomethylene(ethyl)-phosphinate ethyl ester of [12]aneN3 (FIGS. 32A and 32B) are formed almost quantitatively within a few seconds.

The reaction evolves $SO_2$ and $H_2S$ gas, both apparently due to secondary reactions. The yields reported in FIGS. 31 and 32 are isolated yields of the pure compounds. Isolation of the pure product is somewhat more elaborate due to the presence of a large excess of H—P compound and small amounts of the unsubstituted product (10%). Both the monomethylenephosphonate diethyl ester and the monomethylene(ethyl)-phosphinate ethyl ester of [9]aneN3 crystallized in pure form from ethanol. The corresponding [12]aneN3 derivatives are more soluble in ethanol, whereas unsubstituted [12]aneN3 precipitates in ethanol. N-methylation products that are commonly observed as side products in a Mannich reaction involving H—P compounds are not detected in these reactions by $^1H$ NMR.

The reaction mechanism is not clear, but the close proximity of the triiodide group to the sulfonate group must be vital as triiodide can easily be reduced by the excess of H—P compound. The absence of N-methylated products and the low amount of unsubstituted macrocycle present make this method very attractive for preparing monomethylphosphonylated and monomethylphosphinated triazamcrocycles. The yields could undoubtedly be improved by altering the work-up procedure.

EXAMPLE 6

Preparation of Ligands with Two Different Pendent Groups

It is possible to use the pH controlled selectivity of the sulfomethylation reaction to prepare a series of tri- and tetraazacyclomacrocycles with two different types of pendent side-chain chelating groups. The prepared mono and diacetic acid derivatives and monomethylenephosphonate and monomethylenephosphinate derivatives of [12]aneN4, [12]aneN3, and [9]aneN3 make these types of ligands easily available by a synthetic pathway that avoids the use of protective groups. Those skilled in the art will recognize that similar methods may be used to prepare other polyazamacrocycles having different combinations of pendent side-chain groups with desired properties as ligands. Such methods, ligands, and the end uses which determine their desired characteristics are included within the present invention. The following are examples of the general methods applied to candidate macrocycles for illustrative purposes, and are not intended to limit the invention unless so stated.

Figure 33:
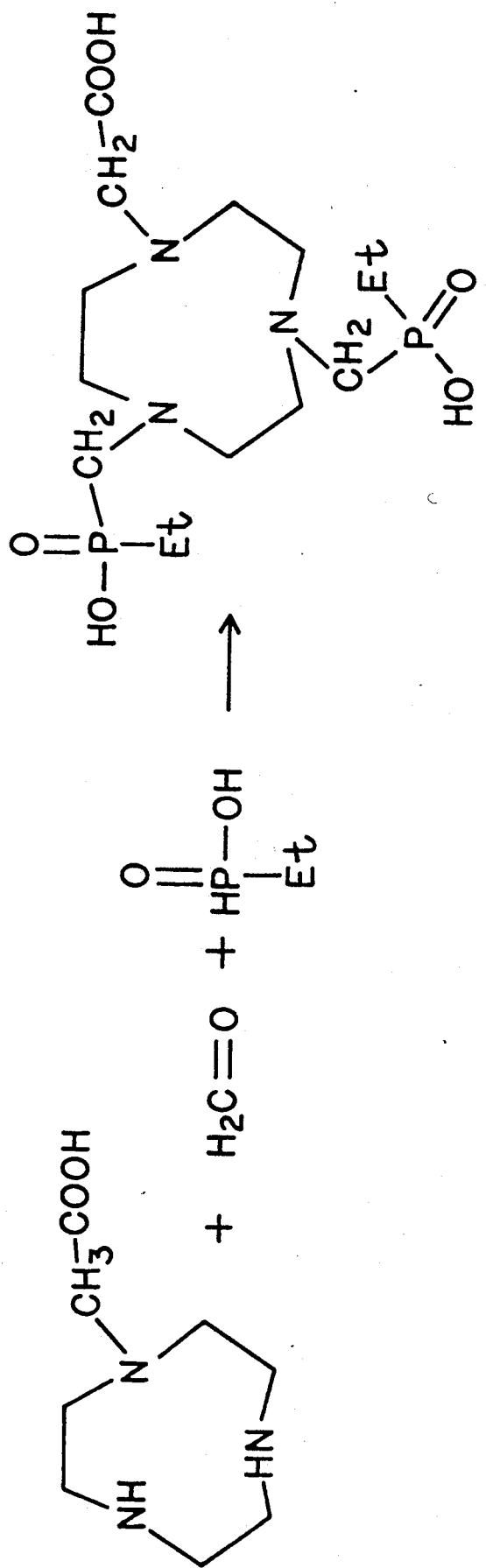
FIG. 33. 1,4,7-triazacyclononane-N-acetic acid is used to prepare triazacyclononane-bis(methylene ethylphosphinate)-monoacetic acid by a Mannich reaction with an acidic solution of formaldehyde and ethylphosphinic acid in 24% yield.
Figure 54:
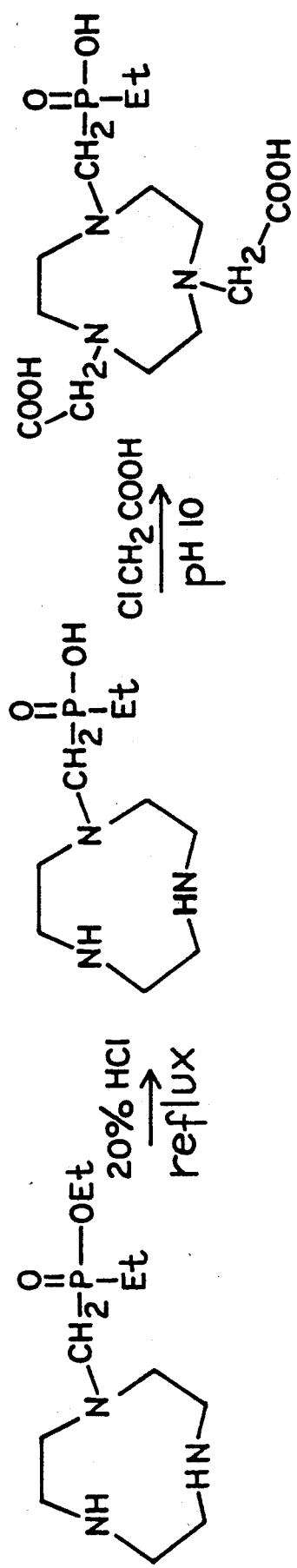

Triazacyclononane-monoacetic acid, the product shown in FIG. 22, is used to prepare triazacyclononane-bis(methylene ethylphosphinate)-monoacetic acid by a Mannich reaction with an acidic solution of formaldehyde and ethylphosphinic acid in 24% yield (FIG. 33). The low yield is largely due to the formation and subsequent separation of N-methylated side products, which apparently cannot be avoided (Tramontini).

This compound is made to compare its complexation characteristics with the similar compound having two acetic acid pendent groups and one methylene-ethylphosphinic acid group. The latter compound is prepared with an overall yield of 37% from the triiodide salt of monosulfomethylated [9]aneN3. 1,4,7-triazacyclononane-N-methylene(ethylphosphinate ethyl ester) was hydrolyzed to yield 1,4,7-triazacyclononane-N-methylene(ethylphosphinic acid), and that product was purified by cation exchange column prior to its reaction with chloroacetic acid (FIG. 34).

Another interesting compound is the monomethylenephosphonate-di(hydroxyethyl) derivative of 1,4,7-triazacyclononane-N,N'-di(2-hydroxyethyl)-N''-methylenephosphonic acid, which is able to form neutral complexes with divalent metal ions. This compound is prepared with a yield of 45% by reaction of oxirane with 1,4,7-triazacyclononane-N-methylenephosphonic acid (FIG. 35). The low yield of this reaction is mainly a result of the extremely hygroscopic product, which makes it difficult to obtain a solid material.

EXAMPLE 7

Preparation of Cyanomethyl, Acetic Acid, and Methylenephosphonate Derivatives of [9aneN3, [12]aneN3 and [12]aneN4

General—The macrocycles 1,4,7-triazacyclononane ([9]aneN3), 1,5,9-triazacyclododecane ([12]aneN3), and [12]aneN3.3 HBr are obtainable from Aldrich and 1,4,7,10-tetraazacyclododecane tetrahydrochloride ([12]aneN4) from Parish Chemical Company. Formaldehyde sodium bisulfite, dichloroethylphosphine, diethylphosphite, and Dowex 50X8-200 ion-exchange resin (100-200 mesh) are obtainable from Aldrich. Dimethylaminomethylenesulfonic acid is prepared in 40% yield with a 92% purity (iodometric assay) according to a modified Backer and Mulder procedure (Backer et al., 1933). 1,4,7-triazacyclononane-N-methylenesulfonate.-HI3, and 1,5,9-triazacyclododecane-N-methylenesulfonate.HI3 are prepared as described previously. A typical product purification is performed by loading the reaction mixture onto a Dowex 50X8 column and eluting the resin with water until the pH of the eluent is neutral. An elution gradient from 0-2.0M HCl is used to wash the product off the column. The fractions (20 mL each) are analyzed by $^1H$ NMR after evaporation. The product fractions are pooled, evaporated under vacuum at 70° C., and the resulting residue is coevaporated with water to remove the excess of HCl. All NMR spectra are recorded on a JEOL FX200 updated with a MacNMR software package; t-butanol is used as internal reference in $D_2O$ samples (1.2 ppm $^1H$ NMR and 31.2 ppm $^{13}C$ NMR). Elemental analyses are performed by Oneida Research Services, Inc.

N-cyanomethyl-1,4,7-triazacyolononane, hydrochloride, the product in FIG. 21. Triazacyclononane (2.32 mmol, 0.300 g) is dissolved in 3 mL water and neutralized with HCl (4.64 mL, 1.0M). Dimethylaminomethylenesulfonic acid (3.20 mmol, 0.485 g) is added to the solution to give a final pH of 3.1. The reaction mixture is stirred for 24 hours at 25° C. Sodium cyanide (3.483 mmol, 0.171 g) is added and the reaction mixture is stirred for another 16 hours at 25° C. The reaction product is purified on Dowex 50X8 (bed volume 25 mL) (see General). To the oily residue 25 mL ethanol is added, yielding the product as a white powder. Yield 33% (0.187 g). $^1H$ NMR ($D_2O$): 4.013 (s, 1H), 3.79 (s, 2H), 3.54 (t, 2H, $^3J=6.1$ Hz), 3.23 (t, 2H, $^3J=6.1$ Hz). $^{13}C$ NMR ($D_2O/H_2O$): 118.0, 49.61, 45.18, 44.04. Anal. Calcd. for $C_8H_{14}N_4.1.5$ HCl.1.5 $H_2O$: C: 38.75, H: 7.52; N: 22.60. Actual: C: 38.99; H: 7.56; N: 22.71.

1,4,7-triazacyclononane-N-acetic acid, hydrochloride, the product in FIG. 22. N-cyanomethyl-1,4,7-triazacyclononane, hydrochloride is prepared as described above starting from [9]aneN3 (3.075 mmol, 0.397 g) and dimethylaminomethylenesulfonic acid (4.61 mmol, 0.642 g) at pH 3.5. Sodium cyanide (4.24 mmol, 0.227 g) is added. After the substitution is complete, the reaction mixture (10 mL) is directly acidified with 4 mL conc. HCl(37%) and heated at 75° C. for 4 days. The solution is evaporated under vacuum. After the addition of 10 mL conc. HCl(37%), NaCl is filtered off. The brownish solution is concentrated to 3 mL. Addition of 3 mL of ethanol to the filtrate gives a white precipitate (0.418 g). The white product is purified using Dowex 50X8 (bed volume 9 mL). Absolute ethanol (10 mL) is added to the residue, whereupon a white solid is formed. The solid is filtered off and washed with ethanol and ether. Yield 32% (0.259 g). $^1$H NMR (D$_2$O): 3.66 (s, 2H), 3.62 (s, 1H), 3.30 (t, 2H, $^3$J=6.1 Hz), 3.09 (t, 2H, $^3$J=61 Hz). $^{13}$C NMR (D$_2$O): 178.40, 57.23, 50.92, 46.36, 45.05. Anal. Calcd. for C$_8$H$_{17}$N$_3$O$_2$.2 HCl: C: 36.93; H: 7.36; N: 16.15. Actual: C: 36.66; H; 7.25; N: 15.8 g.

N,N',N"-tricyanomethyl-1,5,9-triazacyclododecane, FIG. 23. [12]aneN3 (1.52 mmol, 0.26 g) is dissolved in 6.2 mL water and neutralized with a HCl solution (1.32 mL, 1.15M) followed by addition of pH 7 buffer (Metrepak pHydrion tablet: 0.75 g) and formaldehyde sodium bisulfite (6.08 mmol, 0.815 g). The solution is stirred for 16 hours at 25° C. followed by addition of sodium cyanide (6.08 mmol, 0.298 g). The reaction mixture is then heated to 50° C. for 6 hours. The product precipitates from the reaction mixture in pure form. The white precipitate (0.173 g) is filtered off and washed with water (5 mL, 0° C.). The pH of the remaining filtrate is adjusted to 10 by adding a few drops of 1M NaOH and the solution extracted with dichloromethane (3 times 50 mL). After evaporation of dichloromethane, the residue is dissolved in water (5 mL). Small white needle-shaped crystals (0.0702 g) are formed over several hours. The overall yield is 55% (0.243 g, 0.84 mmol). $^1$H NMR (CDCl$_3$): 3.54 (s, 1H), 2.63 (t, 2H), 1.65 (m, 1H), 1.65 (s, 0.3 H, 1 H$_2$O). $^{13}$C NMR (CDCl$_3$): 115.4, 49.2, 42.7, 22.7.

Figure 24:
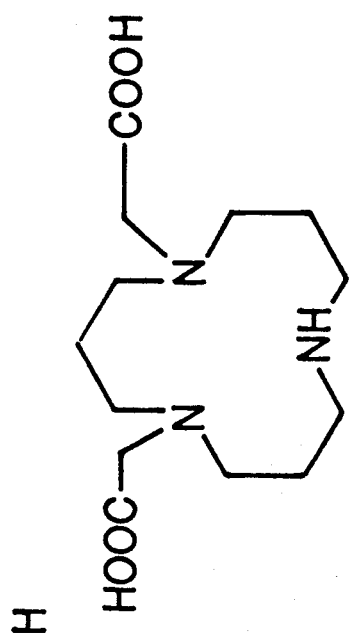
FIG. 24. The tetracyanomethylated derivative of [12]aneN4.

N,N',N", N'''-tetracyanomethyl-1,4,7,10- tetraazacyclododecane, FIG. 24. [12]aneN4 (1.00 mmol, 0.318 g) is dissolved in 2 mL water and neutralized with NaOH (1.34 mL of 1.49M). Formaldehyde sodium bisulfite (5.50 mmol, 0.738 g) is added and the reaction mixture is stirred for 2 hours at 25° C. Sodium cyanide (5.5 mmol, 0.27 g) is added and the reaction mixture is stirred at 25° C. for an additional three days. The white precipitate which forms is filtered off and washed with water (5 mL, 0° C.). The product is dried under vacuum above H$_2$SO$_4$. Yield 61% (0.61 mmol, 0.21 g). $^1$H NMR (CDCl$_3$): 3.59 (s, 1H), 2.76 (s, 2H). $^{13}$C NMR (CDCl$_3$): 114.8, 51.4, 43.54.

Figure 25:
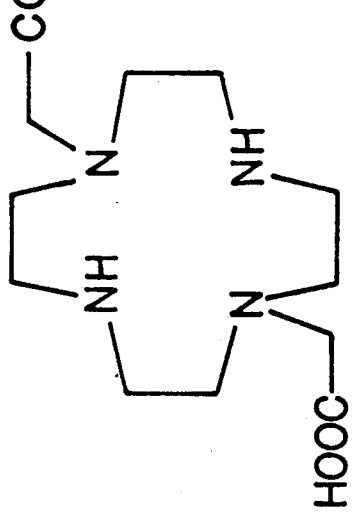
FIG. 25. The 1,7-diacetic acid derivative of [12]aneN4.

1,4,7,10-tetraazacyclododecane-N,N"-diacetic acid, dihydrochloride, FIG. 25. [12]aneN4.4 HCl (1 mmol, 0.318 g) is dissolved in 3 mL water and neutralized with NaOH (1.34 mL, 1.49M). Formaldehyde sodium bisulfite (2.1 mmol, 0.28 g) is added and the solution heated at 40° C. for 16 hours. $^{13}$C NMR indicates that approximately 90% the 1,7-bis(methylenesulfonate) derivative and 10% of the 1,4-isomer is present. Sodium cyanide (2 mmol, 0.098 g) is added. After 6 hours at 25° C. an additional amount of sodium cyanide (0.5 mmol, 0.0243 g) is added an the reaction mixture is stirred for another 16 hours at 25° C. At the end of this period, $^{13}$C NMR shows that the 1,7-bis(cyanomethyl) derivative is formed. $^{13}$C NMR (D$_2$O/H$_2$O): 119.2, 51.52, 45.51, 45.15. The reaction mixture is acidified by adding HCl (37%, 20 mL) and the cyano groups are hydrolyzed by refluxing the solution for 65 hours. The solution is evaporated to dryness under vacuum and coevaporated with 20 mL water (2 times). The product is purified on Dowex 50X8-200 (20 mL bed volume). The product fraction is evaporated under vacuum and lyophilized. 2 mL of ethanol is added to the solid, the white solid filtered and washed with 4 mL ether. Yield 50% (0.190 g). $^{13}$C NMR (D$_2$O/H$_2$O): 176.3, 55.2, 50.75, 44.23. $^1$H NMR (D$_2$O): 3.53 (s, 1H), 3.18 (bs, 2H), 3.06 (bs, 1H), 2.90 (bs, 1H). Anal. Calcd. for C$_{12}$H$_{24}$N$_4$O$_4$.2.5 HCl: C: 37.98; H: 7.04; N: 14.76. Actual: C: 37.87; H: 6.91; N: 14.61.

Figure 26:
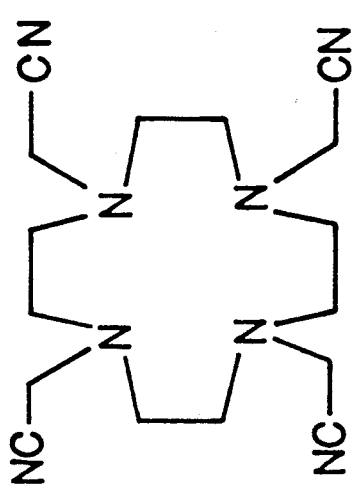
FIG. 26. The diacetic acid derivative of [12]aneN3.

1,5,9-triazacyclododecane-N,N'-diacetic acid, FIG. 26. 1,5,9-triazacyclododecane trihydrobromide (0.414 g, 1 mmol) is dissolved in 3 mL water and neutralized with NaOH (1.342 mL, 1.49M). Formaldehyde sodium bisulfite (0.268 g, 2 mmol) is added and the reaction mixture is heated for 16 hours at 40° C. Sodium cyanide (0.103 g, 2.1 mmol) is added and the mixture is stirred for 24 hours at 25° C. $^{13}$C NMR (D$_2$O/H$_2$O): 117.5, 56.6, 51.1, 50.2, 48.3, 23.2, 22.9. The reaction is worked up by adding NaOH (1.4 mL, 1.49M) and the product is extracted into dichloromethane (100 mL) (three times). The dichloromethane is removed by evaporation under vacuum and the residue is dissolved in 20 mL HCl (20%) and refluxed for 3 days. The solution is evaporated under vacuum and the excess HCl is removed by coevaporation with 10 ML water. The product is purified on Dowex 50X8 (5 mL bed volume). The solid obtained after lyophilization is dissolved in 3 mL ethanol and precipitates upon addition of 20 mL ether. The white solid is filtered off and washed with ether. Yield 19% (0.084 g). $^1$H NMR (D$_2$O): 3.73 (s, 4H), 3.12 (m, 12 H), 2.00 (m, 4H), 1.97 (m, 2H). $^{13}$C NMR (D$_2$O): 172.2, 56.67, 53.92, 52.08, 45.86, 21.84, 21.30. The product is 95% pure as judged by $^{13}$C NMR (a small amount of the monoacetate derivative is present). Anal. Calcd. for C$_{13}$H$_{25}$N$_3$O$_4$.2.5 HCl.3 H$_2$O: C: 36.10; H, 7.81; N: 9.71. Actual: C: 35.87; H: 7.86; N: 9.62.

Figure 30:
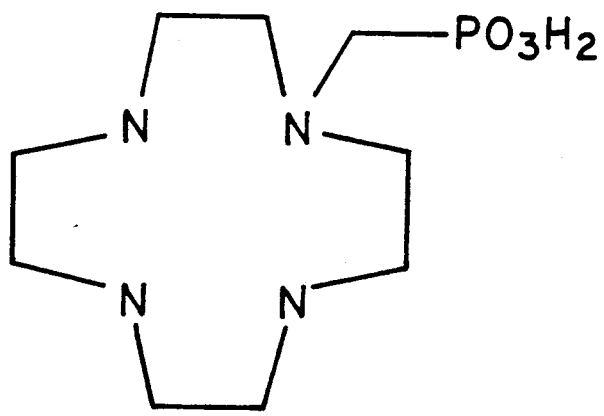
FIG. 30. Monomethylphosphonylated [12]aneN4.

1,4,7,10-tetraazacyclododecane-N-methylenephosphonic acid, FIG. 30. [12]aneN4 (1 mmol, 0.318 g) is dissolved in 3 mL water and neutralized with NaOH (1.40 mL, 1.424M). Formaldehyde sodium bisulfite (0.28 g, 2.1 mmol) is added and the solution is stirred for 16 hours at 40° C. After lyophilization, the resulting solid is added to 4 mL 20% HCl containing iodine (0.51 g, 2 mmol) and NaI (0.30 g, 2 mmol). NaCl precipitates together with a brown gum. After 10 minutes, the solution is filtered over a cotton plug and phosphorous acid (0.82 g, 10 mmol) is added. This solution is boiled for 3 hours. The solution is evaporated to dryness and coevaporated with 20 mL water. The solid is dissolved in 5 mL water and purified on Dowex 50X8 (bed volume 40 mL). The product fraction is evaporated under vacuum and lyophilized. The oily material is treated with ether (10 mL) giving a white powder. Yield 24% (0.103 g). $^1$H NMR (D$_2$O): 3.32 (bs, 4H), 3.28 (bs, 8H), 3.08 (bs, 4H), 2.97 (d, 2H, $^2$J$_{HP}$=9.8 Hz). $^{13}$C NMR (D$_2$O/H$_2$O): 52.46, 50.54, 44.42, 43.98. $^{31}$P NMR (D$_2$O/H$_2$O): 22.92. Anal. Calcd. for C$_9$H$_{23}$N$_4$O$_3$P.4.HCl.0.5 H$_2$O: C: 25.67; H: 6.70; N: 13.30. Actual: C: 25.57; H: 6.74; N: 13.77.

Ethylmonoethylphosphonite, FIG. 36. Dichloroethylphosphine (Caution: Reacts explosively with water at 25° C.) (19.3 g, 0.15 mmol) is added dropwise to 40 mL absolute ethanol and 11.9 mL pyridine at 0° C. within 30 minutes. The reaction mixture is stirred for an additional 30 minutes at 25° C. The pyridine hydrochloride salt that is formed is filtered off prior to distillation of the product under reduced pressure. The product (75°–78° C., 15 mmHg) is obtained in 80% yield (14.8 g, 0.12 mol). $^1$H NMR (CDCl$_3$): 7.06 (d, 1H, $^1J_{HP}$=527 HZ), 4.11 (m, 2H), 1.78 (m, 2H), 1.37 (t, 3H), 1.16 (dt, 3H, $^3J_{HP}$=20 Hz).

1,4,7-triazacyclononane-N-methylenephosphonic acid, FIG. 31A. Phosphorous acid (4.77 g, 58.2 mmol) is melted at 75° C. 1,4,7-triazacyclononane-N-methylenesulfonate.HI$_3$ (1.418 g, 2.34 mmol) is added in small portions under continuous heating at 80° C. After each addition, the brown solid dissolves and rapidly decolorizes. Vapors evolved are likely SO$_2$, H$_2$S, and I$_2$; 5 minutes after the final addition, 15 mL ether is added. The product that precipitates is filtered off and washed with 5 mL of ether. The product is dissolved in 6 mL water and purified on Dowex 50X8 (14 mL bed volume). The oily residue is dissolved in 4 mL water and lyophilized to give a white hygroscopic solid. Yield 21% (0.145 g, 0.48 mmol). $^1$H NMR (D$_2$O) 3.63 (s, 2H), 3.32 (t, 2H, $^3J$=6.1 Hz), 3.11 (t, 2H, $^3J$=6.1 Hz), 3.01 (d, 1H, $^2J_{HP}$=8.6 Hz).

1,4,7-triazacyclononane-N-methylene(ethylphosphinate ethyl ester), FIG. 31B. 1,4,7-triazacyclononane-N-methylenesulfonate.HI$_3$ (0.607 g, 1.00 mmol) is added to 1 mL of ethylmonoethylphosphonite at 0° C. The resulting orange solution is warmed to room temperature; the reaction mixture turns yellow and gases evolve in about 1 minute. 12 mL ethanol is added and the solution is kept at 0° C. for several hours. The white crystals that form are filtered and washed with ethanol (0° C.) and ether (crystals turn light yellow probably as a result of iodide oxidation by ether peroxides). Yield 43% (0.227 g). $^1$H NMR (D$_2$O): 4.15 (dt, 2H), 3.65 (s, 4H), 3.36 (bs, 6H), 3.20 (bt, 4H), 1.98 (m, 2H), 1.35 (t, 3H), 1.14 (dt, 3H, $^3J_{HP}$=18.3 Hz). Anal. Calcd. for C$_{11}$H$_{26}$N$_3$PO$_2$.2 HI.0.33 H$_2$O: C: 25.16; H: 5.50; N: 8.00. Actual: C: 25.12; H: 5.35; N: 7.99. 10 mL ether is added to the filtrate, which gives another precipitate that is filtered off and washed with ether. Yield 0.167 g. This product is less pure as 10% [9]aneN3 and 10% of another phosphorylated product are present, according to $^1$H NMR.

1,4,7-triazacyclononane-N-methylene(phosphonate diethyl ester), FIG. 31C. This compound is prepared using procedures described for 1,4,7-triazacyclononane-N-methylene(ethylphosphinate ethyl ester), starting with 1,4,7-triazacyclononane-N-methylenesulfonate.-HI$_3$ (0.341 g, 0.564 mmol) and diethylphosphite (0.630 mL). After 5 minutes, ethanol (1 mL) is added to the reaction mixture and the product is precipitated from this solution by adding 3 mL of ether during vigorous stirring. The ethanol/ether is decanted and the precipitate is washed with 5 mL ether. The precipitate is dissolved in 1 mL ethanol and crystallized after 10 min. The crystals are filtered off and washed with ether. The precipitate is dissolved in water (5 mL). The pH of the water layer is adjusted to 13 by addition of NaOH. The product is extracted from the water layer with CHCl$_3$ (50 mL). The latter CHCl$_3$ layer is dried with Na$_2$SO$_4$ for several hours before evaporation in vacuum giving a colorless oil. Yield 24% (0.034 g). $^1$H NMR (CDCl$_3$): 4.08 (dt, 4H), 2.97 (d, $^1J_{HP}$=8.5 Hz, 2H), 2.73 (s, 4H), 2.70 (s, 8H), 2.35 (bs, 2H, NH), 1.28 (t, $^3J_{HP}$=7.3 Hz). $^{13}$C NMR(CDCl$_3$): 61.71, 54.65, 52.28 ($^1J_{CP}$=158 Hz), 46.99, 46.38, 16.52.

Figure 32A:
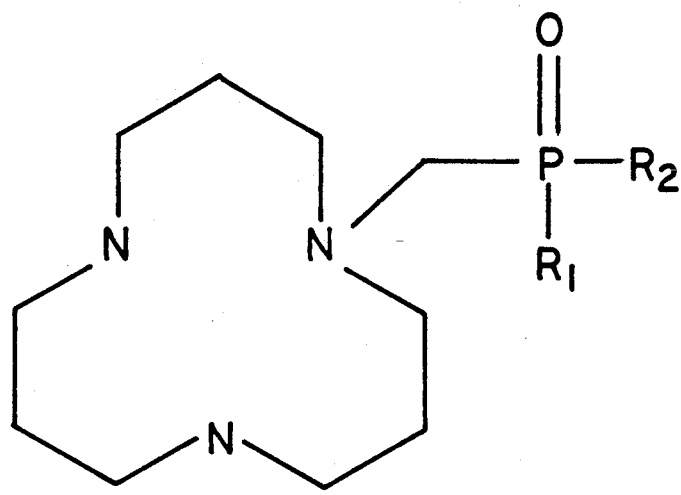
FIGS. 32A and 32B. The monomethylenephosphonate diethyl ester (32A) and the monomethylene(ethyl)phosphinate ethyl ester (32B) of [12]aneN3.

1,5,9-triazacyclododecane-N-methylene(phosphonate diethyl ester), FIG. 32A. Similarly, this compound is prepared as described for 1,4,7-triazacyclononane-N-methylene(phosphonate diethyl ester), starting with 1,5,9-triazacyclododecane-N-methylenesulfonate hydrotriiodide (0.280 g, 0.441 mmol) and 0.625 mL diethylphosphite. The reaction is worked up by addition of 4 mL ether giving a precipitate. The precipitate is washed with 4 mL ether (2 times) and then dissolved in 4 mL ethanol. 1,5,9-triazacyclododecane itself does not dissolve. The precipitate is removed by centrifugation. Ether (4 mL) is added to the clear ethanol solution and the product precipitates. The product is filtered off under nitrogen and is washed with ether (4 mL). The solid is extracted into CHCl$_3$ as described for diethylphosphite. Yield 31% (0.044 g). $^1$H NMR (CDCl$_3$): 4.03 (dt, 4H), 2.69 (m, 16H), 1.57 (m, 6H), 1.24 (t, 6H, $^3J_{HP}$=7.3 Hz). $^{13}$C NMR (CDCl$_3$): 61.25, 53.36, 49.33, 47.19 ($^1J_{HP}$=150.9). 25.78, 25.66, 16.37.

Figure 32B:
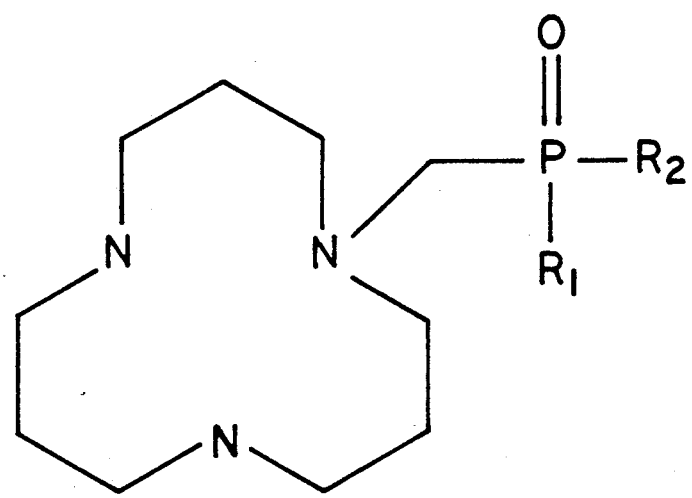

1,5,9-triazacyclododecane-N-methylene)ethylphosphinate ethyl ester), FIG. 32B. This compound is prepared as described for 1,5,9-triazacyclododecane-N-methylene(phosphonate diethyl ester), starting with 1,5,9-triazacyclododecane-N-methylenesulfonate hydrotriiodide (0.314 g, 0.495 mmol) and ethylmonoethylphosphonite (0.625 mL). Yield 73% (0.111 g). $^1$H NMR (CDCl$_3$) 3.96 (dt, 2H), 2.80 (bs, 2H, NH), 2.63 (m, 14H), 1.69 (m, 2H), 1.55 (m, 6H), 1.20 (t, 3H), 1.04 (dt, 3H, $^3J_{HP}$=17.7 Hz). $^{13}$C NMR (CDCl$_3$): 59.90, 52.74, 50.49 ($^1J_{HP}$=104 Hz), 48.63, 46.15, 25.72, 20.82 (($^1J_{CP}$=87.9 Hz), 16.55, 5.65.

1,4,7-triazacyclononane-N,N'-di(methyleneethylphosphinic acid)--N''-acetic acid, hydrochloride, the product in FIG. 33. Dichloroethylphosphine (0.657 mL) is added to 2 g ice under vigorous stirring at 0° C. (Caution: dichloroethylphosphine reacts explosively with water at 25° C.). The solution is slowly warmed to room temperature and triazacyclononane-monoacetic acid is added. During continuous reflux, 3.234 mL of an acidic paraformaldehyde solution (157 mg/ml paraformaldehyde dissolved in 6M hydrochloric acid) is added at a rate of 0.5 mL/hour. This is followed by an additional 16 hours of reflux. The solution is evaporated under vacuum to a very viscous oil which is co-evaporated with 5 mL water followed by 10 mL ethanol. The remaining oil is dissolved in 3 mL ethanol. Most of the ethylphosphinic acid and the dimer of formaldehyde and phosphinic acid are removed by adding 50 mL of ether to the ethanolic solution and decanting the ether/ethanol solution from the sticky gum that is formed. The product is dissolved in 5 mL water and puriried on Dowex 50X8 (bed volume 6 mL). The residue is coevaporated twice with 20 mL ethanol. The remaining oil is dissolved in 1 mL ethanol, and ether (50 mL) is added dropwise to this solution under vigorously stirring. The ether layer is decanted and fresh ether (50 mL) is added and decanted. The ether treatment is repeated twice. The residual ether is evaporated to dryness under vacuum at 70° C. to yield a white, hygroscopic solid. Yield 14% (0.077 g). $^1$H NMR (D$_2$O): 4.06 (s, 2H), 3.46 (s, 8H), 3.41 (s, 4H), 3.39 (d, 4H, $^2J_{HP}$=7.3 Hz), 1.76 (m, 4H), 1.08 (dt, 6H, $^3J$=7.9 Hz, $^3J_{HP}$=18.3 Hz). Anal. Calcd. for C$_{14}$H$_{31}$N$_3$P$_2$O$_6$.3 HCl.1.5 H$_2$O: C: 31.39; H: 6.96; N: 7.84. Actual: C: 31.28; H: 6.72; N: 7.60.

b  1,4,7-triazacyclononane-N-methylene(ethylphosphinic acid)-N',N''-diacetic acid, the final product in FIG. 34. 1,4,7-triazacyclononane-N-methylene(ethylphosphinate ethyl ester) is prepared as described above starting from 1,4,7-triazacyclononane-N-methylenesulfonate.HI$_3$ (4.942 g, 8.17 mmol) and 6 mL of ethylmonoethylphosphonite. The product is precipitated by addition of 8 mL ethanol and 40 mL ether. After filtration, the light yellow solid (4.02 g) is dissolved in 20% HCl (30 mL) and refluxed for 6 hours. This solution is evaporated under vacuum and the residue is coevaporated with water (30 mL). The residue is dissolved in 6 mL water and purified on Dowex 50X8 (bed volume 33 mL). The residue is dissolved in ethanol (50 mL), and concentrated under vacuum to 5 mL. The addition of acetone (150 mL) gives a white precipitate. The white solid obtained by decanting is dissolved in 10 mL ethanol, and 200 mL acetone is added dropwise while the solution is stirred vigorously. The white solid is dried under vacuum at 70° C. to give pure 1,4,7-triazacyclononane-N-methylene(ethylphosphinic acid), the intermediate product in FIG. 34, (1.183 g) as a white foam. $^1$H NMR (D$_2$O): 3.49 (s, 4H), 3.17 (t, 4H, $^3J=6.1$ Hz), 2.98 (t, 4H, $^3J=6.1$ Hz), 2.92 (d, 2H, $^2J_{HP}=2$ Hz), 1.55 (m, 2H), 0.92 (dt, 3H, $^3J_{HP}=24$ Hz, $^3J=8$ Hz). The solid is dissolved in 10 mL water and neutralized with NaOH (5.7 mL, 1.527M). Chloroacetic acid (1.65 g, 17.42 mmol) is added and the pH is adjusted to 10.5 and maintained at this value by addition of NaOH (1.527M). The reaction mixture is heated at 70° C. for 16 hours. After cooling to room temperature, HCl (1.0M) is added to adjust the pH to 7. The reaction mixture is evaporated to dryness and HCl(37%) is added. The NaCl that forms is filtered off. The HCl solution is evaporated under vacuum and coevaporated with 20 mL water. The residue is dissolved in 10 mL ethanol and 100 mL ether is added dropwise with vigorous stirring to remove the excess chloroacetic acid and hydroxyacetic acid that forms during the reaction. A white precipitate is collected by decantation, washed with ether (2X100 mL), and dried under vacuum at 70° C. for 1 hour. Yield 37% (1.446 g). $^1$H NMR (D$_2$O): 4.01 (s, 4H), 3.47 (s, 4H), 3.42 (bs, 8H), 3.35 (d, 2H, $^2J_{HP}=5.5$ Hz), 1.73 (m, 2H), 1.08 (dt, 3H, $^3J_{HP}=13.8$ Hz, J=7.9 Hz). Anal. Calcd. for C$_{13}$N$_{26}$N$_3$PO$_6$.2 HCl.0.5 CH$_3$CH$_2$OH.0.65 NaCl: C: 34.65; H: 6.44; N: 8.66. Actual: C: 34.63; H: 6.46; N: 8.66.

1,4,7-triazaoyclononane-N,N'-di(2-hydroxyethyl)-N''-methylenephosphonic acid, the product in FIG. 35. The monomethylenephosphonate of [9]aneN3 (0.145 g, 0.48 mmol) is dissolved in 1.5 mL water and NaOH (1.00 mL, 1.424M) is added to adjust the pH of the solution to 10. Oxirane (0.044 g, 1 mmol) is added. After 16 hours at 25° C., additional oxirane (0.009 g, 0.2 mmol) is added to complete the reaction. This is stirred an additional 24 hours at room temperature. The resulting mixture is acidified with 1.0 mL HCl(37%). Upon addition of 2 mL ethanol, NaCl precipitates and is filtered off. Another ethanol treatment (5 mL) gives additional NaCl. The filtrate is evaporated under vacuum to yield a viscous oil, which is dissolved in 4 mL water. The product is purified on Dowex 50X8 (bed volume 5 mL). The residue is dissolved in 4 mL water and lyophilized. 5 mL acetone is added to the lyophilized material and the resulting solid is filtered off and washed with ether. Yield 45% (0.090 g, 0.214 mmol). The solid is extremely hygroscopic. $^1$H NMR (D$_2$O): 3.98 (bt, 4H), 3.79 (s, 4H), 3.48 (m, 8H), 3.22 (bt, 4H), 3.00 (d, 2H, $^2J_{HP}=10.0$ Hz). Anal. Calcd. for C$_{11}$H$_{26}$N$_3$PO$_5$.2 HCl.2 H$_2$O: C: 31.44; H: 7.67; N: 10.00. Actual: C: 31.51; H: 7.30; N: 10.21.

REFERENCES

The following references are incorporated in pertinent part by reference herein for the reasons cited in the specification.

Alcock, N. W. et al., *J. Chem. Soc., Chem. Commun.,* 1989, 629.
Backer, H. J. et al., *Recl. Trav. Chim. Pays-Bas,* 1933, 52, 454.
Backer, H. J. et al., *Recl. Trav. Chim. Pays-Bas,* 1934, 53, 1120.
Bucherer, H., et al., *Chem. Ber.,* 1906, 39, 2810.
Burg, A. B. *Inorg. Chem.,* 1989, 28, 1295.
Cortes, S. et al., *Inorg. Chem.* 1990, 29, 5.
Cox, J. P. L. et al., *Chem. Soc. Perkin Trans* 1, 1990, 2567.
Delgado, R. et al., *Helv. Chim. Acta* 1990, 73, 140.
Desreux, J. F. et al., *Inorg. Chem.* 1981, 20, 987.
Dischino, D. D. et al., *Inorg. Chem.* 1991, 30, 1265.
Falk, R. A. et al. *J. Am. Oil Chemists' Soc.,* 1958, 35, 171.
Geraldes, C. F. G. C. et al., *Inorg. Chem.* 1989, 28, 3336.
Geraldes, C. F. G. C. et al., *Chem. Soc. Perkin Trans.* 2, 1991, 137.
Gilbert, E. E. 'Sulfonation and related reactions', Ch. 5, Interscience, New York, 1965.
Hama, H. et al., *Nippon Kaguku Kaishi* 1975, 1182.
Kimura, E. et al., *Am. Chem. Soc.,* 1981, 103, 3041.
Knoevenagel, A., *Chem. Ber.,* 1904, 37, 1.
Knoevenagel, E., *Chem. Ber.* 1904, 89, 4073.
Kruper, W. J., Jr., Eur. Pat. Appl. EP 374,929. Chem. Abstr. 114:6547.
Lauffer, R. B. *Chem. Rev.,* 1987, 87, 901
Miller, W. V. et al., *Chem. Ber.* 1892, 25, 2032.
Neelakantan, I. et al., *J. Org. Chem.,* 1959, 24, 1943.
Neves, A. et al., *J. Inorg. Chem.* 1988, 27, 2484.
Parker, D. et al., Eur. Pat. Appl.
Polikarpov, Yu. M. et al., *Izv. Akad. Nauk SSSR, Ser. Khim.* 1982, 7, 1669.
Ramasamy, R. *FEBS Let.,* 1991, 280, 121.
Reinking, E. et al. *Chem. Ber.,* 1905, 38, 1069.
Smith, R. M.; Martell, A. E. eds., 'Critical Stability Constants' Vol. 6. plenum Press, New York and London 1989.
Smith, R. et al. *J. Org. Chem.* 1950, 15, 46.
Stetter, H. et al., *R. Tetrahedron* 1981, 37, 767.
Stewart, T. D. et al., *J. Am. Chem. Soc.,* 1932, 54, 4173, 4183.
Strecker, W. *Ann.* 1850, 75, 27.
Studer, M. et al., *Helv. Chim. Acta,* 1986, 69, 2081.
Tramontini, M., *Synthesis,* 1973, 703
Tweedle, M. F. et al., Eur. Pat. Appl. EP 232,751 1987. Chem. Abstr. 108:56130.
Ulrich, H. et al., U.S. Pat. No. 2,205,995, CA 34: 7298.
van Westrenen, J. et al., manuscript in preparation.
Yang, R. et al., *Inorg. Chem.* 1976, 15, 1499.
Zompa, L. J., *Inorg. Chem.,* 1978, 17, 2631.
Zompa, L. J., *Inorg. Chem.,* 1976, 15, 1499.

Changes may be made in the construction, operation and arrangement of the various reactants, steps and procedures described herein without departing from the concept and scope of the invention as defined in the following claims.

ABBREVIATIONS

MRI—magnetic resonance imaging

NMR—nuclear magnetic resonance
[9]aneN3—triazacyclononane
[12]aneN3—triazacyclododecane
[12]aneN4—tetraazacyclododecane
[18]aneN6—hexaazacyclooctadecane
formaldehyde sodium bisulfite is used in this application to indicate the adduct formed by the reaction of formaldehyde and sodium bisulfite, viz., hydroxymethylenesulfonate

What is claimed is:

1. A MRI contrast agent consisting essentially of a complex of a paramagnetic lanthanide (III) cation with 1,4,7,10-tetraazacyclododecane-(N,N''-diacetic acid)-(N'-R$^1$)-(N'''-R$^2$) or salt thereof, where R$^1$ and R$^2$ are independently selected from the group consisting of

 (a)

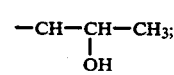 (b)

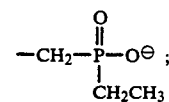 (c)

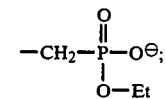 (d)

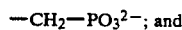 and (e)

 (f)

2. A MRI contrast agent consisting essentially of a complex of a paramagnetic lanthanide (III) cation with 1,4,7,10-tetraazacyclododecane-(N,N''-diacetic acid)-(N'-R$^1$)-(N'''-R$^2$) or salt thereof, where R$^1$ and R$^2$ are independently selected from the group consisting of

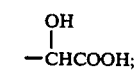 (a)

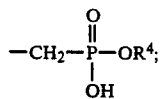 (b)

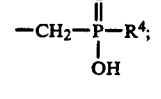 (c)

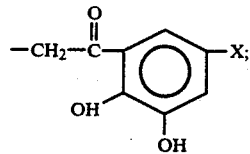 (d)

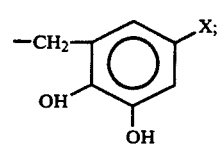 (e)

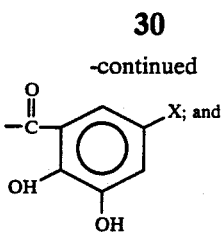 (f)

where R$^4$ is —C$_q$H$_{2q+1}$; X is selected from the group consisting of —SO$_3$H and, —COOH; and q is 2–10.

3. A NMR shift reagent consisting essentially of a paramagnetic lanthanide cation exclusive of gadolinium complexed with 1,4,7,10-tetraazacyclododecane-(N,N''-diacetic acid)-(N'-R$^1$)-(R'''-R$^2$) or salt thereof, where R$^1$ and R$^2$ are independently selected from the group consisting of

 (a)

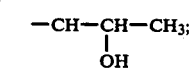 (b)

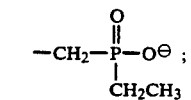 (c)

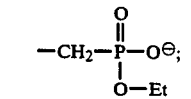 (d)

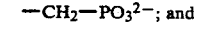 and (e)

 (f)

4. A NMR shift reagent comprising a paramagnetic lanthanide cation exclusive of gadolinium complexed with 1,4,7,10-tetraazacyclododecane-(N,N''-diacetic acid)-(N'-R$^1$)-(N'''-R$^2$), where R$^1$ and R$^2$ are independently selected from the group consisting of

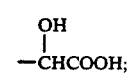 (a)

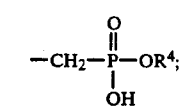 (b)

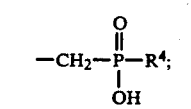 (c)

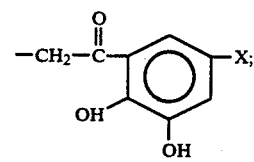 (d)

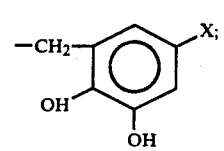 (e)

-continued

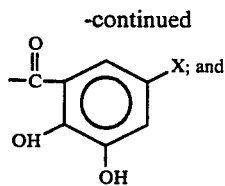 (f)

where R⁴ is —$C_qH_{2q+1}$; X is selected from the group consisting of —$SO_3H$, —COOH, and salts thereof; and q is 2–10.

5. 1,4,7,10-Tetraazacyclododecane-N,N'''-diacetic acid.

6. 1,4,7,10,13,16-Hexaazacyclooctadecane-N,N'', N''''-triacetic acid.

7. A MRI contrast agent consisting essentially of a complex of a paramagnetic lanthanide (III) cation with 1,4,7,10,13,16-hexaazacyclooctadecane-(N,N'',N''''-triacetic acid)-(N'-R¹)-(N'''-R²)-(N'''''-R³) or salt thereof, where R¹, R² and R³ are independently selected from the group consisting of:

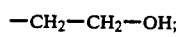 (a)

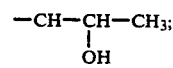 (b)

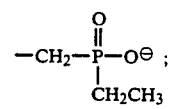 (c)

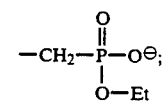 (d)

—$CH_2$—$PO_3^{2-}$; and (e)

—H. (f)

8. A MRI contrast agent consisting essentially of a complex of a paramagnetic lanthanide (III) cation with 1,4,7,10,13,16-hexaazacyclooctadecane-(N,N'',N''''-triacetic acid)-(N'-R¹)-(N'''-R²)-(N'''''-R³) or salt thereof, where R¹, R² and R³ are independently selected from the group consisting of:

—$(CH_2)_q$COOH; (a)

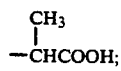 (b)

 (c)

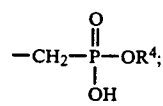 (d)

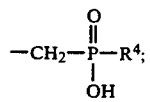 (e)

-continued

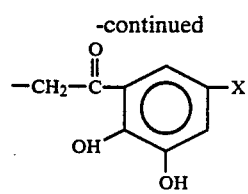 (f)

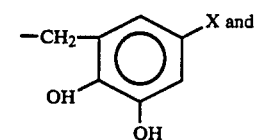 (g)

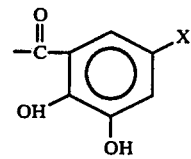 (h)

where R⁴ is —$C_qH_{2q+1}$; X is selected from the group consisting of —$SO_3H$ and —COOH; and q is 2–10.

9. The agent of claims 7 or 8 where the lanthanide (III) cation is gadolinium (III).

10. A NMR shift reagent consisting essentially of a paramagnetic lanthanide cation exclusive of gadolinium complexed with 1,4,7,10,13,16-hexaazacyclooctadecane-(N,N'',N''''-triacetic acid)-(N'-R¹)-(N'''-R²)-(N'''''-R³) or salt thereof, where R¹, R² and R³ are independently selected from the group consisting of:

—$CH_2$—$CH_2$—OH; (a)

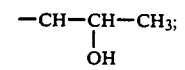 (b)

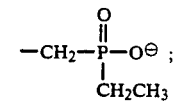 (c)

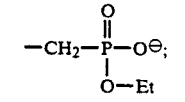 (d)

—$CH_2$—$PO_3^{2-}$; and (e)

—H. (f)

11. A NMR shift reagent consisting essentially of a paramagnetic lanthanide cation exclusive of gadolinium complexed with 1,4,7,10,13,16-hexaazacyclooctadecane-(N,N'',N''''-triacetic acid)-(N'-R¹)-(N'''-R²)-(N'''''-R³) or salt thereof, where R¹, R² and R³ are independently selected from the group consisting of:

—$(CH_2)_q$COOH; (a)

 (b)

 (c)

-continued
(d) 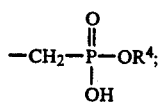
(e) 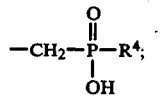
(f) 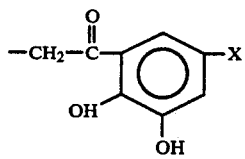
-continued
(g) 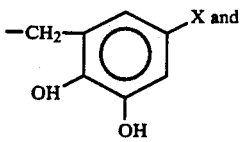
(h) 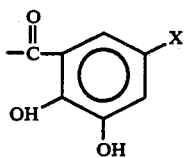
where $R^4$ is $-C_qH_{2q+1}$; X is selected from the group consisting of $-SO_3H$ and $-COOH$; and Q is 2-10.
* * * * *

UNITED STATES PATENT AND TRADEMARK OFFICE
CERTIFICATE OF CORRECTION

PATENT NO. : 5,316,757
DATED : May 31, 1994
INVENTOR(S) : A. Dean Sherry, Jeroen van Westrenen It is certified that error appears in the above-indentified patent and that said Letters Patent is hereby corrected as shown below:

In claim 1, line 20, column 29: Change the first occurence of "CH" to --$CH_2$--.

In claim 3, line 15, column 30: Change "R'''" to --N--.

In claim 3, line 21, column 30: Change the first occurence of "CH" to --$CH_2$--.

In claim 7, line 27, column 31: Change the first occurence of "CH" to --$CH_2$--.

In claim 10, line 37, column 32: Change the first occurence of "CH" to --$CH_2$--.

In claim 11, line 17, column 34: Change the "Q" to --$q$--.

Signed and Sealed this

Thirty-first Day of October 1995

*Attest:*

BRUCE LEHMAN

*Attesting Officer*    Commissioner of Patents and Trademarks